US010279348B2

(12) United States Patent
Miki et al.

(10) Patent No.: US 10,279,348 B2
(45) Date of Patent: May 7, 2019

(54) SEMICONDUCTOR MICRO-ANALYSIS CHIP AND METHOD OF MANUFACTURING THE SAME

(71) Applicant: KABUSHIKI KAISHA TOSHIBA, Minato-ku, Tokyo (JP)

(72) Inventors: Hiroko Miki, Kawasaki (JP); Hideto Furuyama, Yokohama (JP); Kentaro Kobayashi, Tokyo (JP); Akihiro Kojima, Nonoichi (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 475 days.

(21) Appl. No.: 14/198,425

(22) Filed: Mar. 5, 2014

(65) Prior Publication Data
US 2015/0041316 A1 Feb. 12, 2015

(30) Foreign Application Priority Data
Aug. 12, 2013 (JP) .................................. 2013-167649

(51) Int. Cl.
*B01D 57/02* (2006.01)
*B01D 61/46* (2006.01)
(Continued)

(52) U.S. Cl.
CPC .... *B01L 3/502753* (2013.01); *G01N 15/1031* (2013.01); *G01N 15/1484* (2013.01);
(Continued)

(58) Field of Classification Search
USPC ............... 422/422, 502, 503, 513, 534, 535; 204/450, 518, 572, 627, 640
See application file for complete search history.

(56) References Cited

U.S. PATENT DOCUMENTS 6,096,656 A * 8/2000 Matzke ............... B81C 1/00071
   205/122
6,444,173 B1 * 9/2002 Sjursen ................. B01L 3/0268
   204/600
(Continued)

FOREIGN PATENT DOCUMENTS

CN          1720438 A    1/2006
CN        101960313 A    1/2011
(Continued)

OTHER PUBLICATIONS

Separation of Long DNA Molecules in a Microfabricated Entropic Trap Array, Science 288 (5468), 1026-1029. J. Han and H. G. Craighead (Year: 2000).*
(Continued)

*Primary Examiner* — Dean Kwak
(74) *Attorney, Agent, or Firm* — Holtz, Holtz & Volek PC

(57) ABSTRACT

One of embodiments is a semiconductor micro-analysis chip for detecting particles in a sample liquid. The chip comprises a semiconductor substrate, a first flow channel provided on the semiconductor substrate to allow the sample liquid to flow therein, a second flow channel provided at a different position from the first flow channel of the semiconductor substrate to allow the sample liquid or an electrolyte solution to flow therein, a contact portion where a portion of the first flow channel and a portion of the second flow channel abut each other or intersect one another with a partition being arranged between the flow channels, and a fine hole provided on the partition of the contact portion to allow the particles to pass therethrough.

17 Claims, 22 Drawing Sheets

(51) Int. Cl.
  *B01L 3/00* (2006.01)
  *G01N 15/10* (2006.01)
  *G01N 15/14* (2006.01)
  *G01N 15/00* (2006.01)

(52) U.S. Cl.
  CPC ............ *B01L 2200/0647* (2013.01); *B01L 2300/0645* (2013.01); *B01L 2300/0681* (2013.01); *B01L 2400/086* (2013.01); *G01N 2015/0053* (2013.01); *G01N 2015/1006* (2013.01); *G01N 2015/1486* (2013.01)

(56) References Cited

U.S. PATENT DOCUMENTS

| | | | |
|---|---|---|---|
| 6,537,437 B1* | 3/2003 | Galambos | B01J 19/0093 204/600 |
| 7,297,151 B2 | 11/2007 | Boecker et al. | |
| 7,390,388 B2 | 6/2008 | Childers et al. | |
| 7,604,592 B2 | 10/2009 | Freeman et al. | |
| 7,651,600 B2* | 1/2010 | Han | G01N 27/44791 204/601 |
| 7,837,379 B2* | 11/2010 | Fiering | B01F 5/0641 137/599.03 |
| 7,883,665 B2 | 2/2011 | Aizenberg et al. | |
| 7,977,122 B2 | 7/2011 | Sandoz et al. | |
| 8,158,410 B2* | 4/2012 | Tang | G01N 1/40 422/50 |
| 8,182,635 B2 | 5/2012 | Ayliffe et al. | |
| 8,329,016 B1* | 12/2012 | Sommer | G01N 27/44747 204/605 |
| 8,343,425 B1* | 1/2013 | Li | B01F 13/0061 422/502 |
| 8,409,523 B2 | 4/2013 | Mendel-Hartvig et al. | |
| 8,608,891 B2 | 12/2013 | Ayliffe et al. | |
| 8,722,423 B2 | 5/2014 | Bergman et al. | |
| 8,759,115 B2 | 6/2014 | Ohman et al. | |
| 8,821,812 B2 | 9/2014 | Ohman et al. | |
| 8,974,749 B2 | 3/2015 | Bergman et al. | |
| 8,986,524 B2* | 3/2015 | Afzali-Ardakani | B82Y 15/00 204/403.01 |
| 2003/0040173 A1 | 2/2003 | Fonash et al. | |
| 2003/0119034 A1* | 6/2003 | Kang | B01L 3/502761 435/6.11 |
| 2004/0053422 A1 | 3/2004 | Chan et al. | |
| 2004/0144658 A1 | 7/2004 | Flory | |
| 2005/0019784 A1 | 1/2005 | Su et al. | |
| 2005/0042766 A1* | 2/2005 | Ohman | B01L 3/50273 436/174 |
| 2006/0000772 A1* | 1/2006 | Sano | B01D 67/0062 210/635 |
| 2006/0035386 A1* | 2/2006 | Hattori | B01D 29/00 436/514 |
| 2006/0073489 A1 | 4/2006 | Li et al. | |
| 2007/0242560 A1 | 10/2007 | Norikane et al. | |
| 2008/0278728 A1 | 11/2008 | Tetz et al. | |
| 2008/0311375 A1 | 12/2008 | Harnack et al. | |
| 2009/0120796 A1* | 5/2009 | Han | B01L 3/502707 204/518 |
| 2009/0136958 A1 | 5/2009 | Gershow et al. | |
| 2009/0194429 A1 | 8/2009 | Hibbs et al. | |
| 2009/0208920 A1 | 8/2009 | Öhman et al. | |
| 2011/0000561 A1 | 1/2011 | Asogawa et al. | |
| 2011/0030888 A1 | 2/2011 | Ayliffe et al. | |
| 2011/0071051 A1 | 3/2011 | Halter et al. | |
| 2011/0081677 A1* | 4/2011 | Luo | B01L 3/502753 435/41 |
| 2011/0162439 A1* | 7/2011 | Ayliffe | B01L 3/502715 73/61.71 |
| 2011/0291026 A1 | 12/2011 | Renna et al. | |
| 2012/0043202 A1 | 2/2012 | Miyamura et al. | |
| 2012/0115130 A1 | 5/2012 | Imai et al. | |
| 2012/0142904 A1 | 6/2012 | He et al. | |
| 2012/0228730 A1 | 9/2012 | Akiyama et al. | |
| 2012/0258479 A1 | 10/2012 | Ding et al. | |
| 2012/0292496 A1 | 11/2012 | Escobedo et al. | |
| 2013/0002438 A1 | 1/2013 | Känsäkoski et al. | |
| 2013/0065777 A1 | 3/2013 | Altug et al. | |
| 2014/0057311 A1* | 2/2014 | Kamm | B01L 3/502753 435/29 |
| 2014/0158540 A1 | 6/2014 | Ohura | |
| 2015/0308977 A1 | 10/2015 | Saito et al. | |

FOREIGN PATENT DOCUMENTS

| | | |
|---|---|---|
| CN | 102047103 A | 5/2011 |
| CN | 102804242 A | 11/2012 |
| CN | 103718029 A | 4/2014 |
| JP | 2001088096 A | 4/2001 |
| JP | 2003315349 A | 11/2003 |
| JP | 2004219370 A | 8/2004 |
| JP | 2004317340 A | 11/2004 |
| JP | 2004325304 A | 11/2004 |
| JP | 2004354364 A | 12/2004 |
| JP | 2005098818 A | 4/2005 |
| JP | 2005230647 A | 9/2005 |
| JP | 2005532151 A | 10/2005 |
| JP | 2006090910 A | 4/2006 |
| JP | 2006130400 A | 5/2006 |
| JP | 2007090135 A | 4/2007 |
| JP | 2007170840 A | 7/2007 |
| JP | 2008039541 A | 2/2008 |
| JP | 4366327 B2 | 11/2009 |
| JP | 2009264904 A | 11/2009 |
| JP | 2009541737 A | 11/2009 |
| JP | 2010185703 A | 8/2010 |
| JP | 2010187664 A | 9/2010 |
| JP | 2011516884 A | 5/2011 |
| JP | 2012042426 A | 3/2012 |
| JP | 2012255810 A | 12/2012 |
| JP | 2013036865 A | 2/2013 |
| JP | 2014521956 A | 8/2014 |
| TW | 200415346 A | 8/2004 |
| TW | 200528389 A | 9/2005 |
| TW | 200638037 A | 11/2006 |
| TW | 200712494 A | 4/2007 |
| WO | 2009126257 A1 | 10/2009 |
| WO | 2013016486 A1 | 1/2013 |
| WO | 2013137209 A1 | 9/2013 |

OTHER PUBLICATIONS

Entropic trapping and sieving of long DNA molecules in a nanofluidic channel, Journal of Vacuum Science & Technology A 17, 2142 (1999). J. Han, and H. G. Craighead (Year: 1999).*
Taiwanese Office Action (and English translation thereof) dated Feb. 18, 2016, issued in counterpart Taiwanese Application No. 103126025.
International Search Report and Written Opinion dated Oct. 21, 2014 issued in counterpart International Application No. PCT/JP2014/068848.
U.S. Appl. No. 14/012,566, First Named Inventor: Kentaro Kobayashi, Title: "Semiconductor Micro-Analysis Chip and Manufacturing Method Thereof", filed Aug. 28, 2013.
U.S. Appl. No. 14/011,640, First Named Inventor: Kentaro Kobayashi, Title: "Semiconductor Micro-Analysis Chip and Sample Liquid Flowing Method", filed Aug. 27, 2013.
U.S. Appl. No. 14/012,599, First Named Inventor: Kentaro Kobayashi, Title: "Semiconductor Analysis Microchip and Method of Manufacturing the Same", filed Aug. 28, 2013.
U.S. Appl. No. 14/011,666, First Named Inventor: Sadato Hongo, Title: "Sample Detection Apparatus and Detection Method", filed Aug. 27, 2013.
Japanese Office Action (and English translation thereof) dated Aug. 16, 2016, issued in counterpart Japanese Application No. 2013-167649.

* cited by examiner

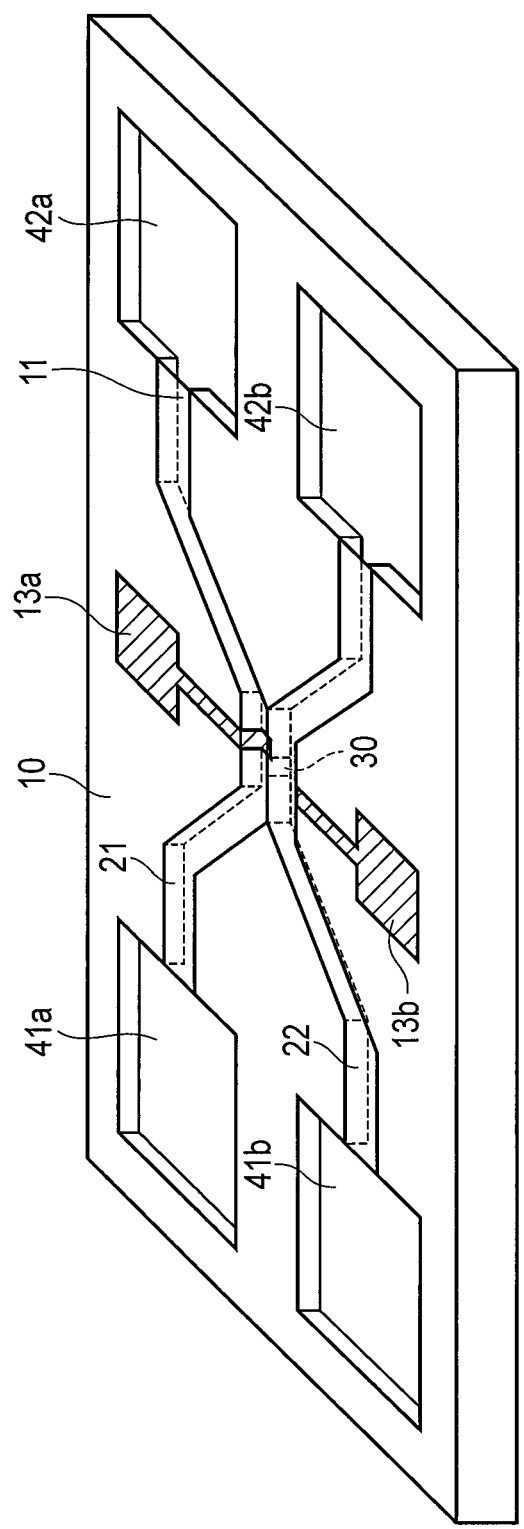
F I G. 2

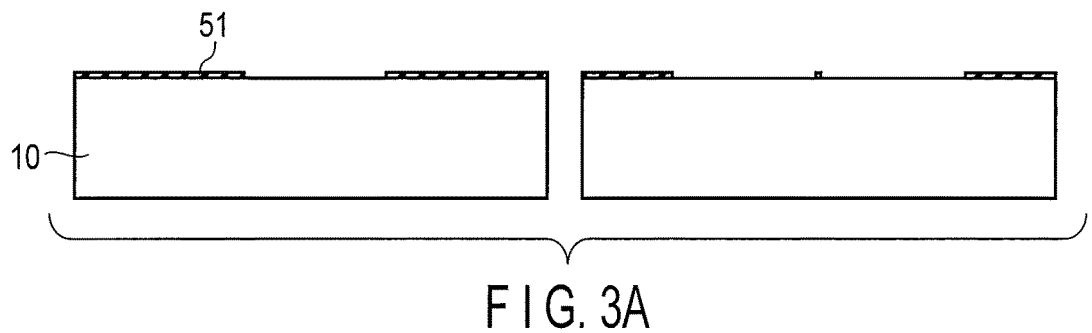
F I G. 3A
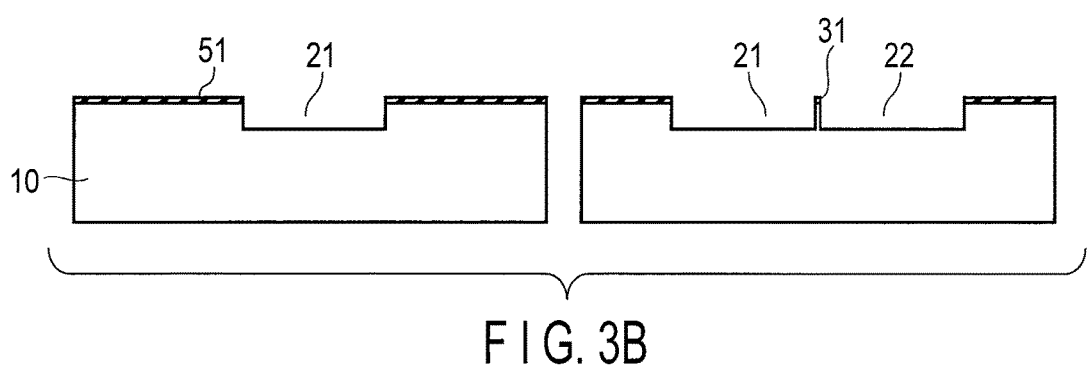
F I G. 3B
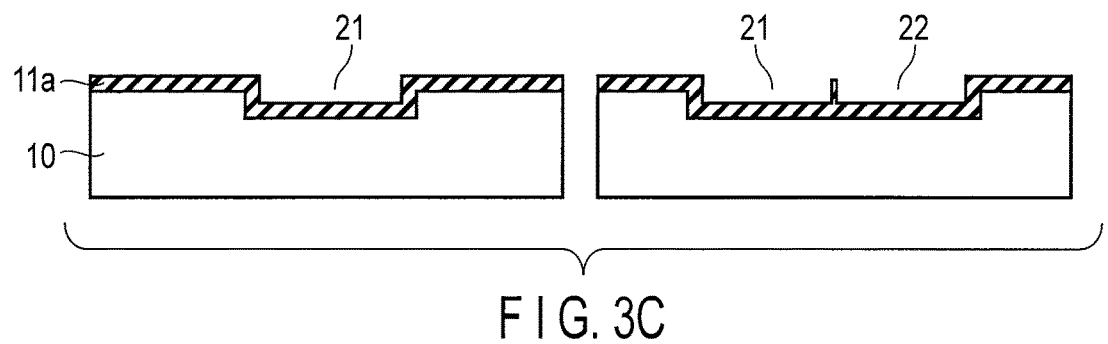
F I G. 3C
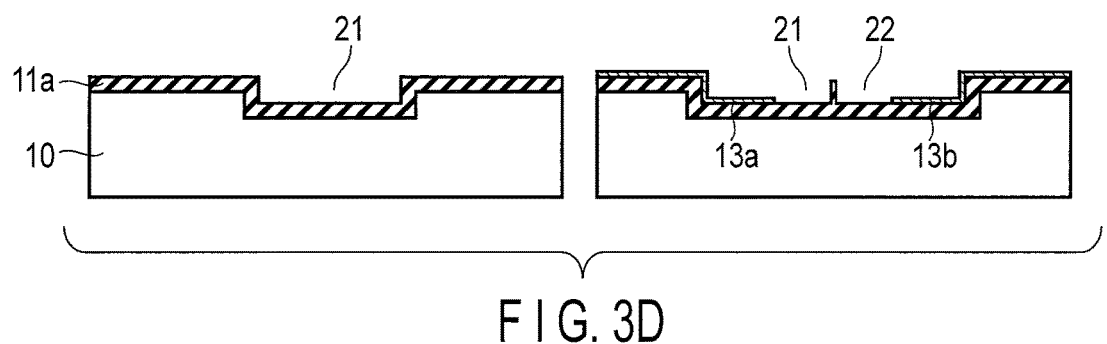
F I G. 3D

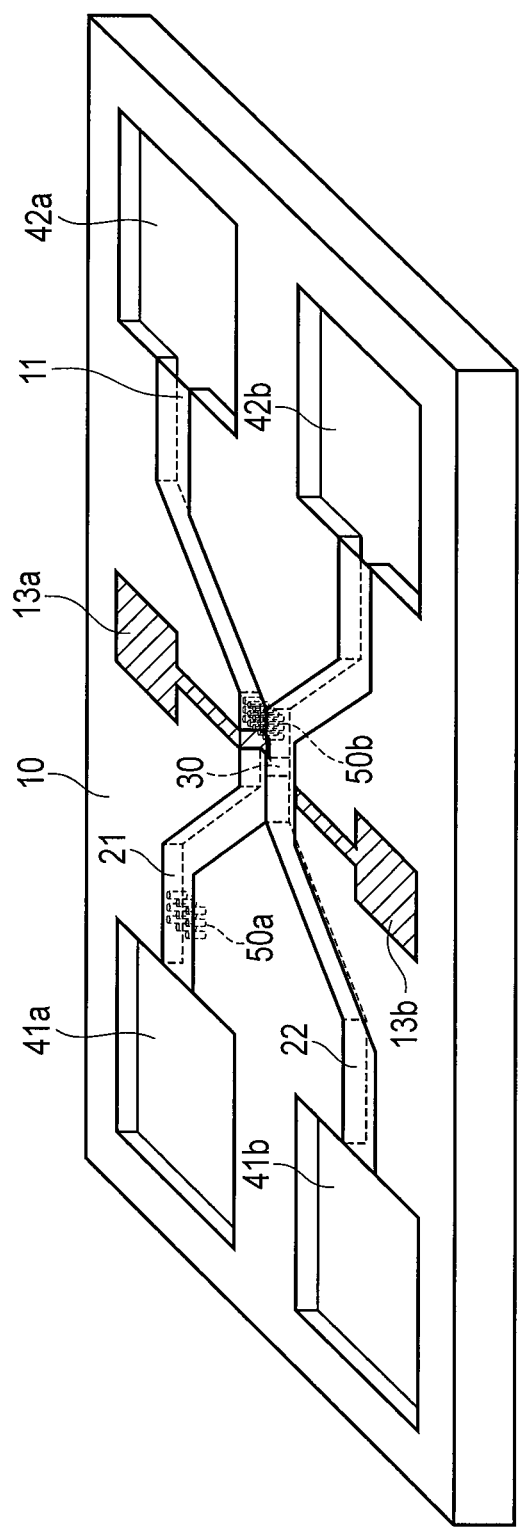
F I G. 5

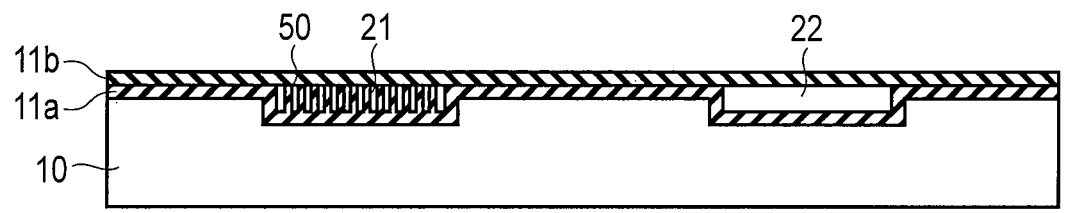
F I G. 6
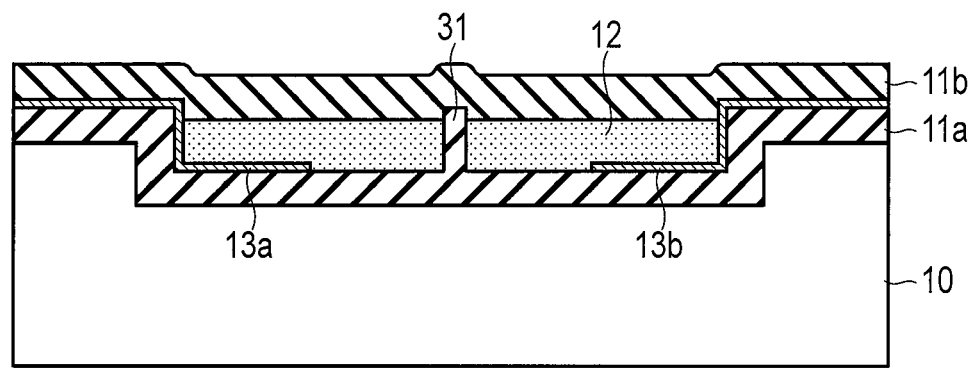
F I G. 7A
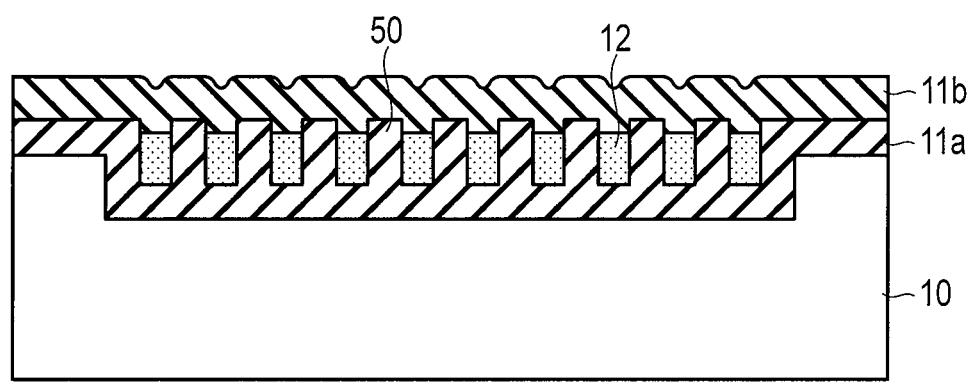
F I G. 7B

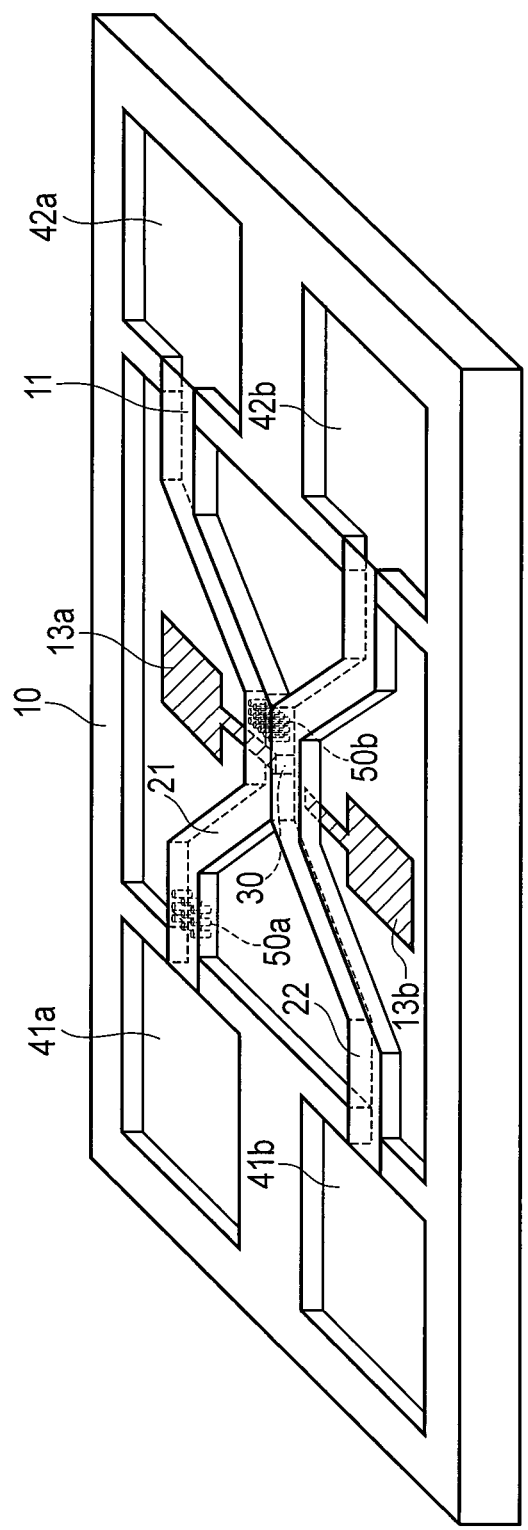
F I G. 10

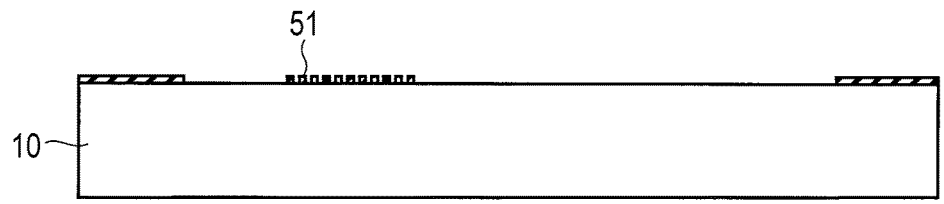
F I G. 11A
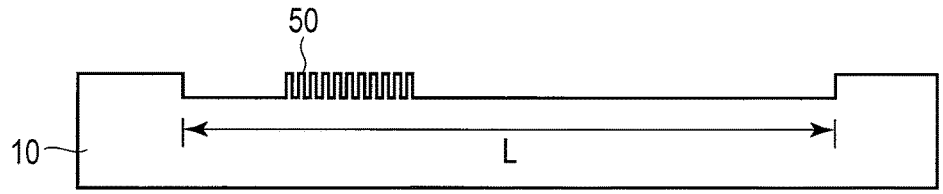
F I G. 11B
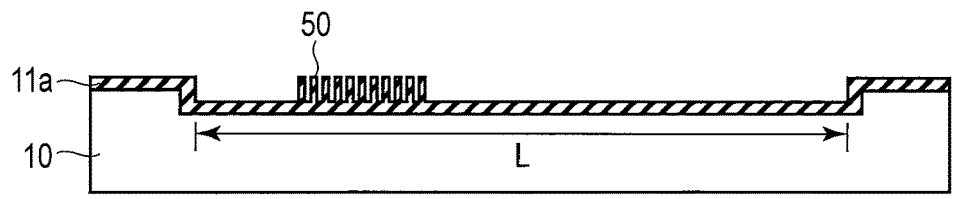
F I G. 11C
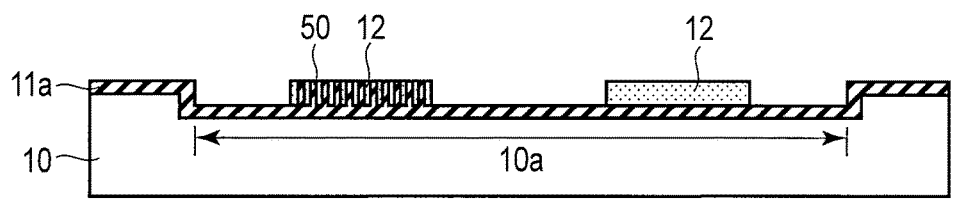
F I G. 11D
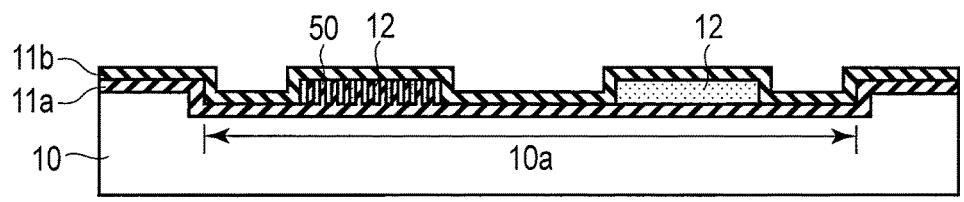
F I G. 11E
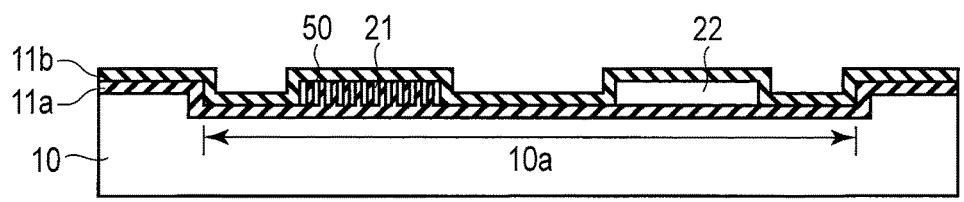
F I G. 11F

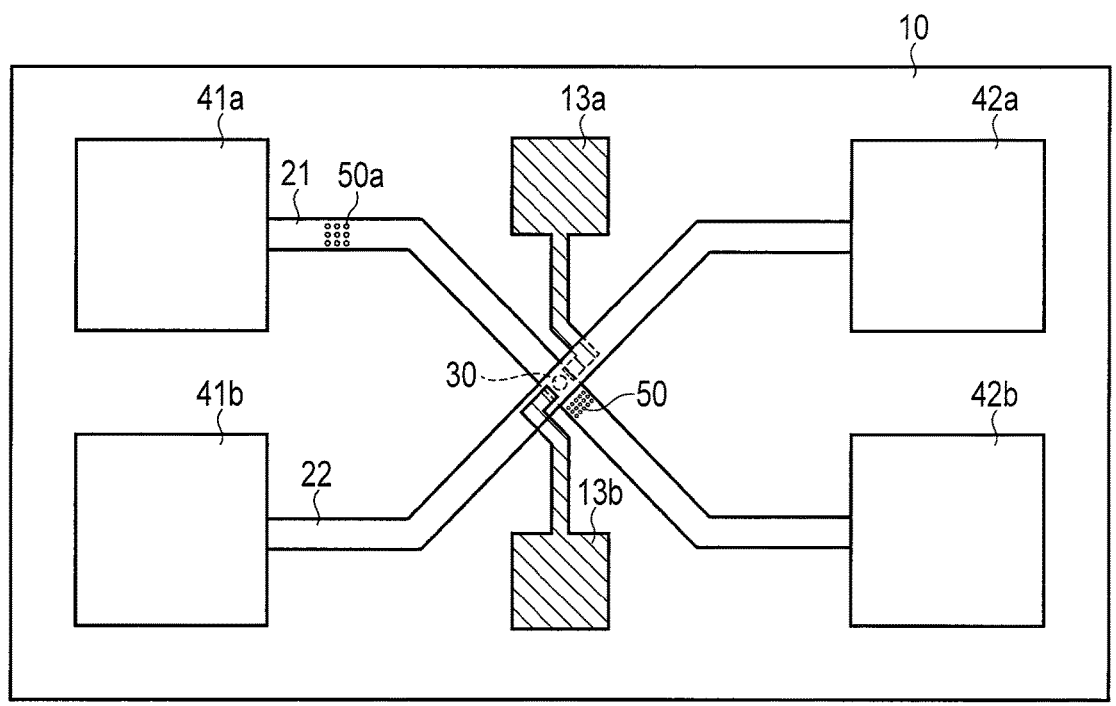
F I G. 12

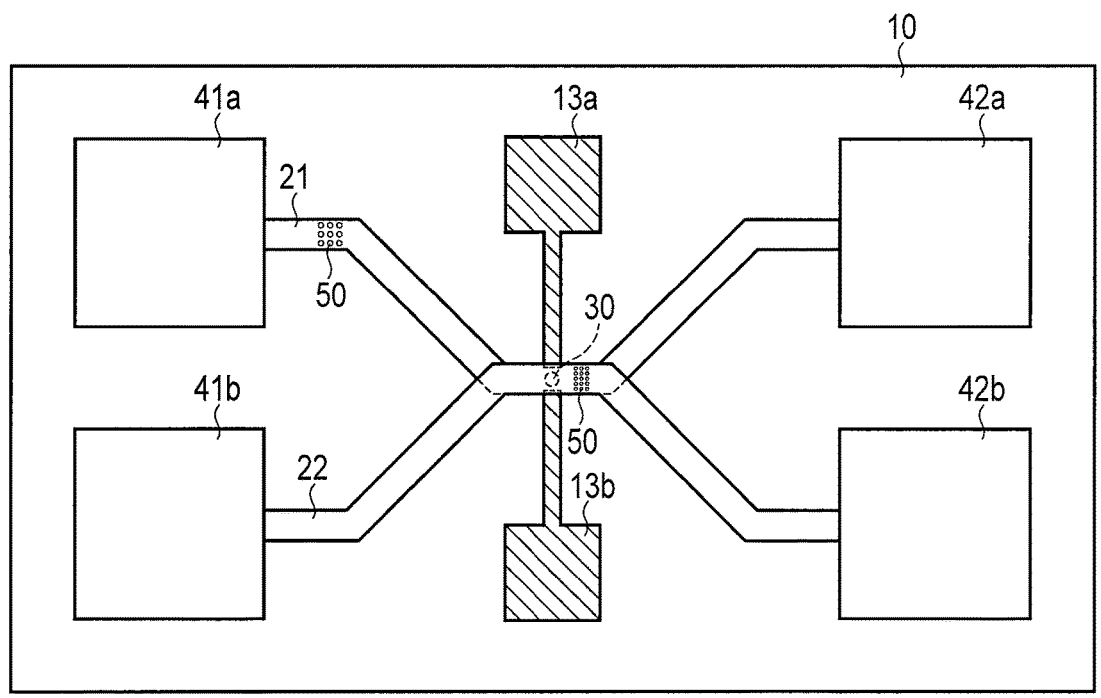
F I G. 15

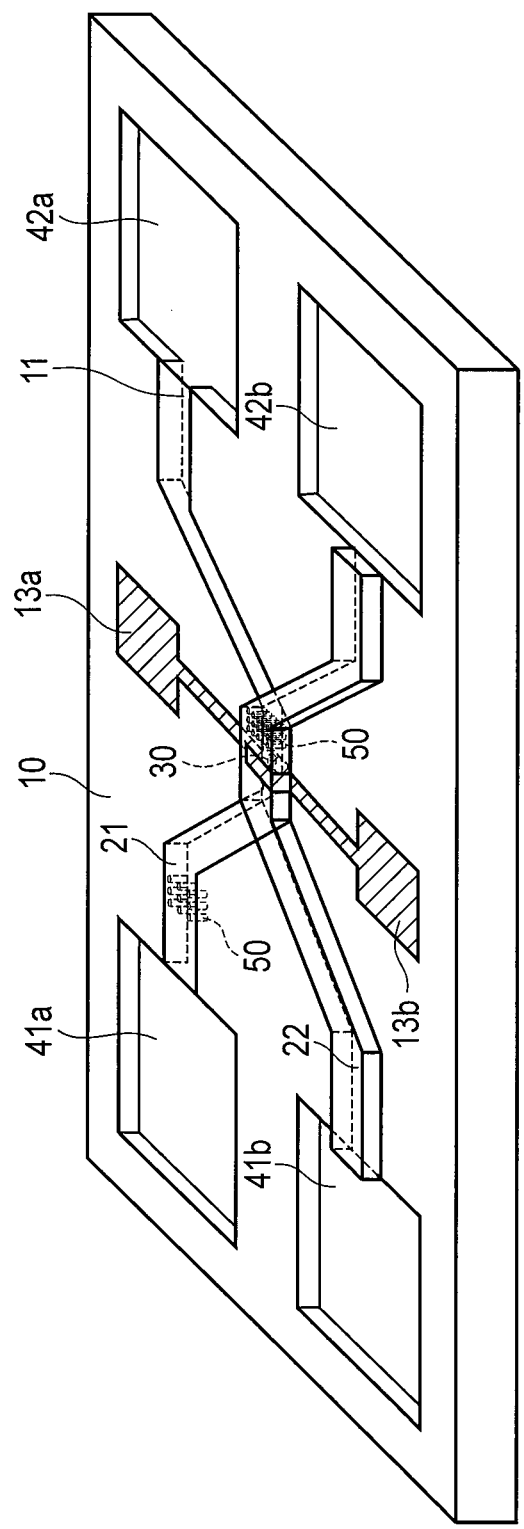
F I G. 16

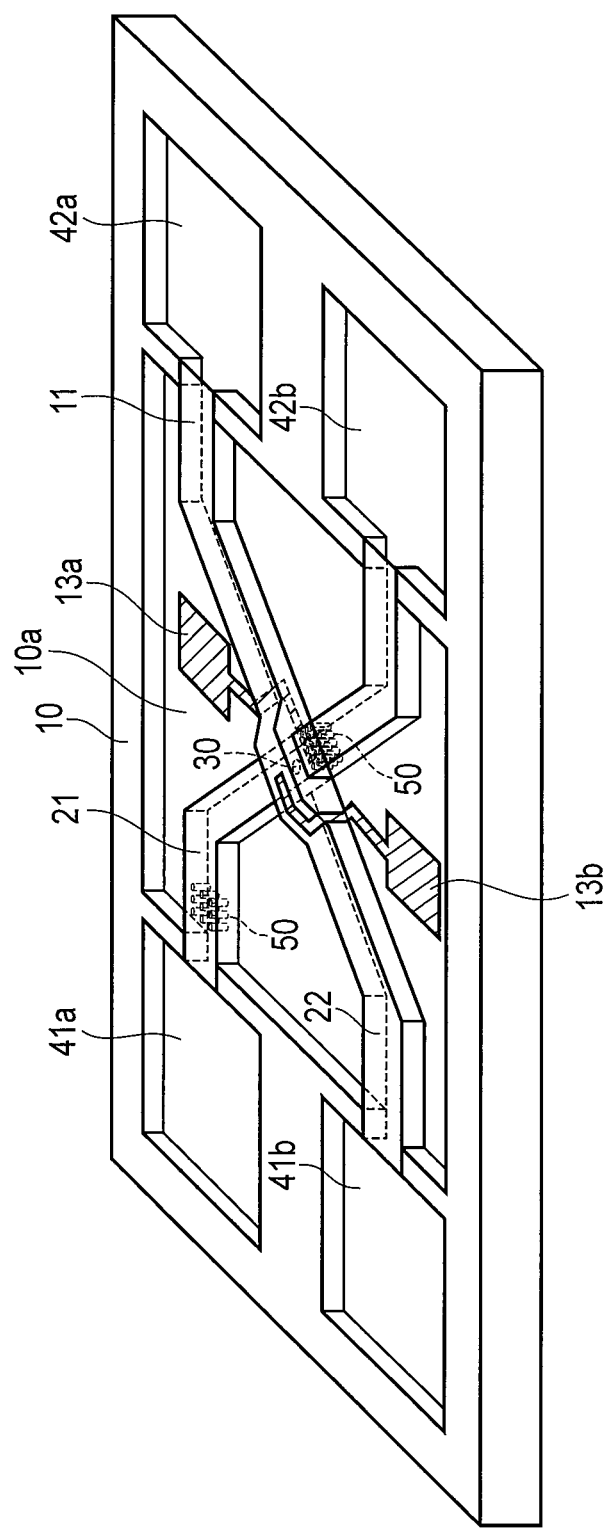
F I G. 19

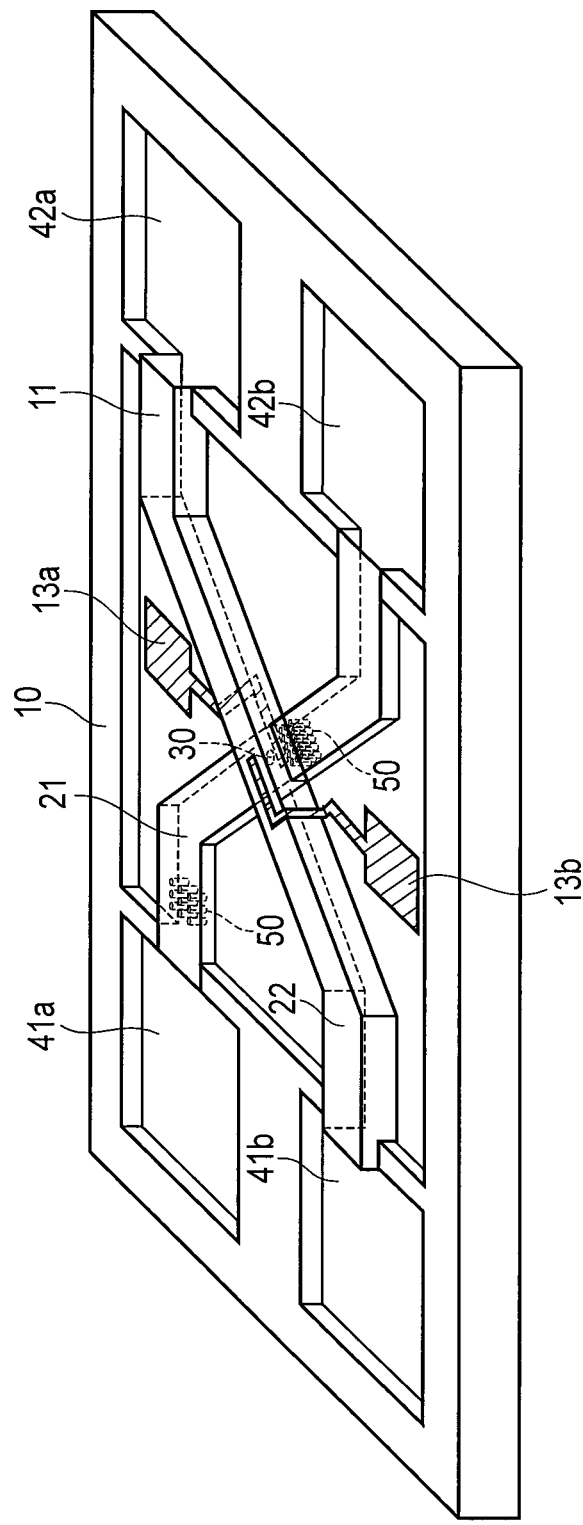
F I G. 20

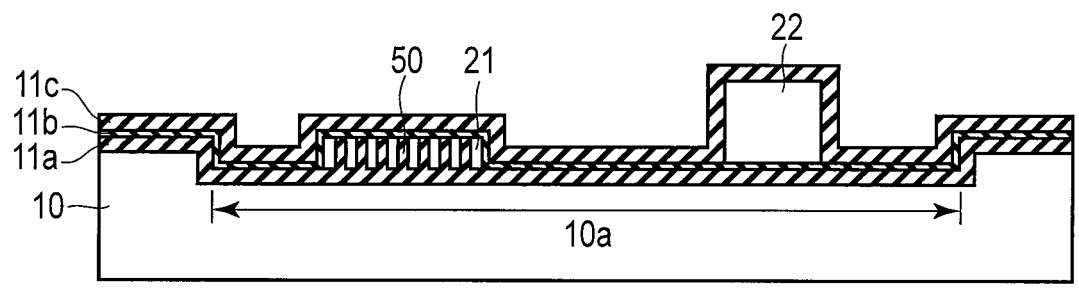
F I G. 21A
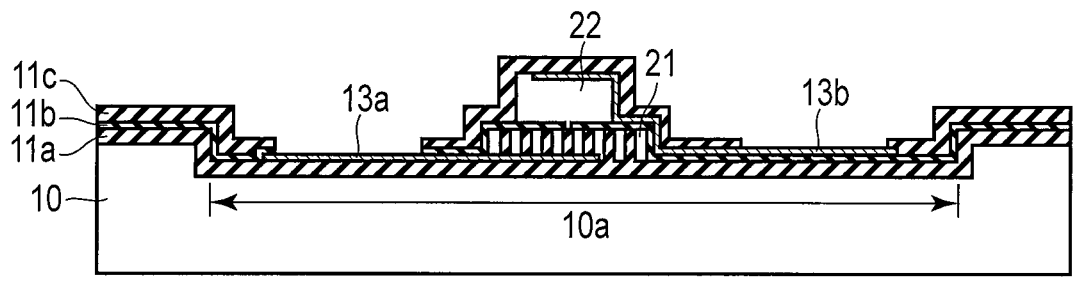
F I G. 21B

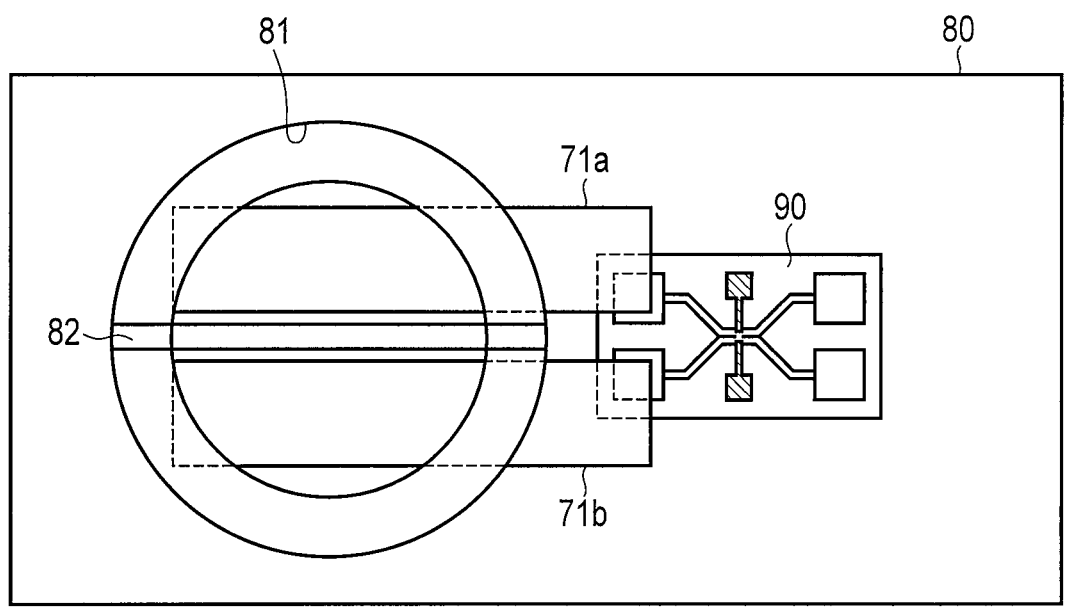
F I G. 23

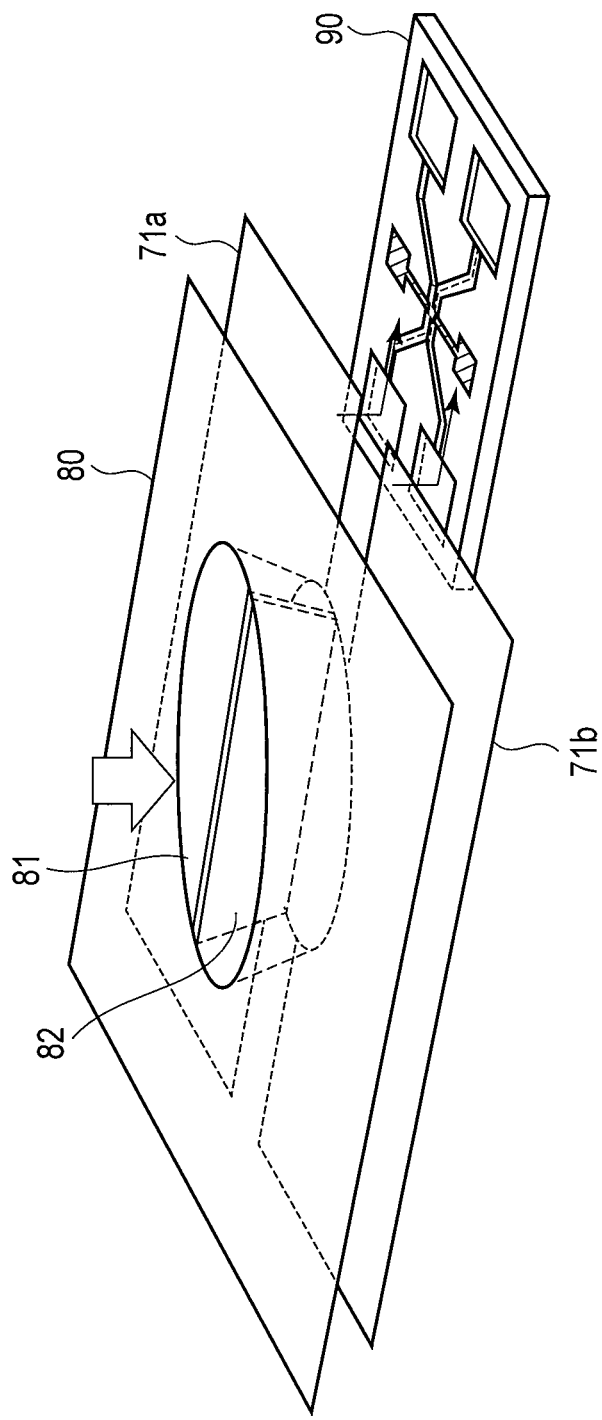
F I G. 24

US 10,279,348 B2

SEMICONDUCTOR MICRO-ANALYSIS CHIP AND METHOD OF MANUFACTURING THE SAME

CROSS-REFERENCE TO RELATED APPLICATIONS

This application is based upon and claims the benefit of priority from Japanese Patent Application No. 2013-167649, filed Aug. 12, 2013, the entire contents of which are incorporated herein by reference.

FIELD

Embodiments described herein relate generally to a semiconductor micro-analysis chip capable of detecting a particulate sample, and a method of manufacturing the same.

BACKGROUND

Recently, in the technical fields of biotechnology, healthcare, and so on, micro-analysis chips having elements such as fine flow channels and detection systems integrated thereon have been used. These micro-analysis chips often have tunnel flow channels formed by providing covers over fine grooves formed on glass substrates or resin substrates. As a sensing method, counting fine particles using fine holes is known other than laser light scattering and fluorescent detection.

BRIEF DESCRIPTION OF THE DRAWINGS

FIG. 2 is a perspective view showing a schematic structure of the semiconductor micro-analysis chip of the first embodiment;

FIGS. 3A to 3G are cross-sectional views showing a process of manufacturing the semiconductor micro-analysis chip of the first embodiment;

FIG. 5 is a perspective view showing a schematic structure of the semiconductor micro-analysis chip of the second embodiment;

FIG. 6 is a cross-sectional view showing a schematic structure of the semiconductor micro-analysis chip of the second embodiment;

FIGS. 7A and 7B are cross-sectional views showing over-etching of a sacrifice layer;

FIG. 10 is a perspective view showing a schematic structure of a semiconductor micro-analysis chip of a third embodiment;

FIGS. 11A to 11F are cross-sectional views showing a process of manufacturing the semiconductor micro-analysis chip of the third embodiment;

FIG. 12 is a plan view showing a schematic structure of a semiconductor micro-analysis chip of a fourth embodiment;

FIG. 15 is a plan view showing a modified example of the fourth embodiment;

FIG. 16 is a perspective view showing a modified example of the fourth embodiment;

FIG. 19 is a perspective view showing a schematic structure of a semiconductor micro-analysis chip of a fifth embodiment;

FIG. 20 is a perspective view showing a schematic structure of a semiconductor micro-analysis chip of a sixth embodiment;

FIGS. 21A and 21B are cross-sectional views showing the schematic structure of the semiconductor micro-analysis chip of the sixth embodiment;

FIG. 23 is a plan view showing a schematic structure of a semiconductor micro-analysis chip of an eighth embodiment; and FIG. 24 is a perspective view showing the schematic structure of the semiconductor micro-analysis chip of the eighth embodiment.

DETAILED DESCRIPTION

Figure 1:
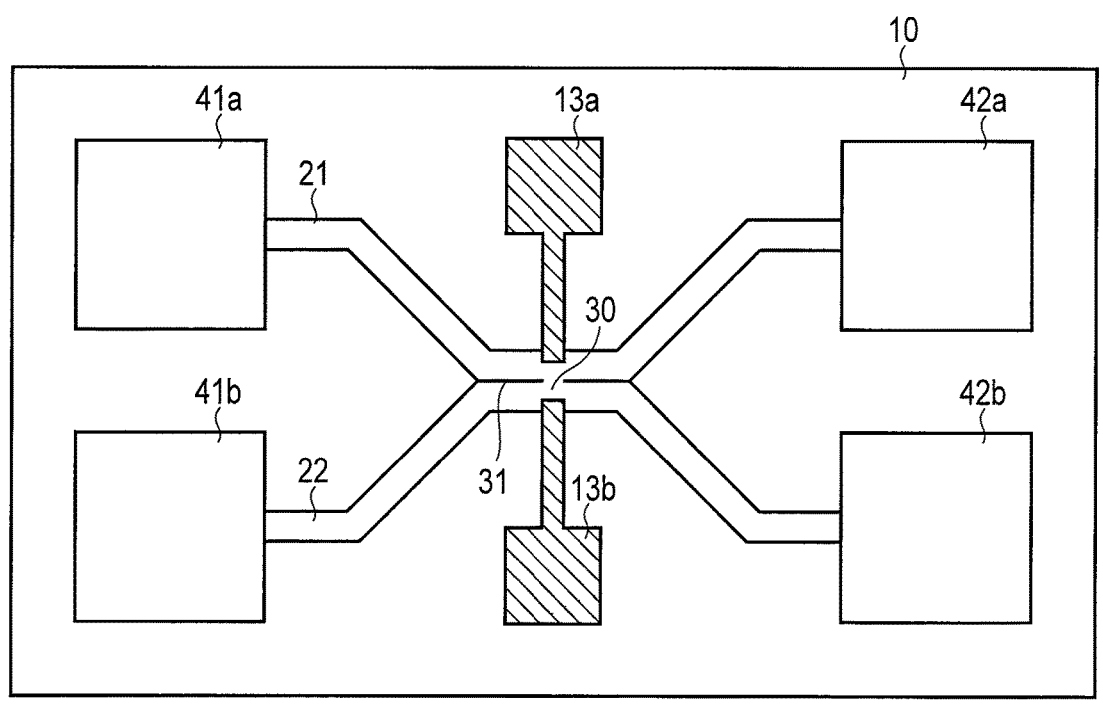
FIG. 1 is a plan view showing a schematic structure of a semiconductor micro-analysis chip of a first embodiment.

In general, according to one embodiment, a semiconductor micro-analysis chip for detecting particles in a sample liquid comprises: a semiconductor substrate; a first flow channel provided on the semiconductor substrate, into which the sample liquid is introduced; a second flow channel provided at a position different from the first flow channel of the semiconductor substrate, into which the sample liquid or an electrolyte solution is introduced; a contact portion where a portion of the first flow channel and a portion of the second flow channel abut each other or intersect one another with a partition being arranged between the first flow channel and the second flow channel; and a fine hole provided on the partition of the contact portion and configured for the fine particles in the sample liquid to pass.

The semiconductor micro-analysis chip is fabricated by integrating small flow channels and a fine particle detection mechanism on the semiconductor substrate. The sample liquid (i.e., suspension liquid obtained by dispersing fine particles in an electrolyte solution) is introduced to the sample liquid inlet of the first flow channel and the sample liquid or an electrolyte is introduced to the sample liquid inlet of the second flow channel, and then the flow channels are filled with each liquid. When the particles pass through the fine hole arranged between the first flow channel and the second flow channel, an ion current variation through the fine hole occurs, so observing the ion current variation the particles can be electrically detected.

The semiconductor micro-analysis chip is made of a semiconductor wafer such as Si, and then mass production technology with semiconductor fabrication process technology can be utilized. For this reason, semiconductor micro-analysis chips can be remarkably miniaturized and manufactured in large quantity as compared with a micro-analysis chip using a quartz substrate or a resin substrate frequently adopted in prior art. A large number of semiconductor micro-analysis chips can be therefore manufactured at low costs. In addition, the semiconductor micro-analysis chips according to this embodiment do not require bonding process of another substrate or a cover glass to form a sealing structure (lid) of the flow channels. Furthermore, ultra-compact chips and high sensitive detection can be achieved by introducing a novel structure such as three-dimensional arrangement of flow channels, which has been difficult according to prior art. Since the particles are to be detected electrically, noise separation from detection signals by utilizing electronic circuit technology and the high sensitive detection with real-time digital processing (statistic processing, etc.) can be achieved. Moreover, a detection system can be drastically compact as compared with an optical detection system because the micro-analysis chip does not require equipment such as an optical system which occupies much space.

The embodiments will be hereinafter described with reference to the accompanying drawings. Some specific materials and structures are exemplified below, but materials and structures having the same functions as those can be employed similarly and are not limited to those of the embodiments described below.

(First Embodiment)

FIG. 1 is a top view schematically illustrating a semiconductor micro-analysis chip of a first embodiment, and FIG. 2 is a perspective view showing the schematic structure of the semiconductor micro-analysis chip.

In the figures, 10 denotes a semiconductor substrate. Various semiconductors of Si, Ge, SiC, GaAs, InP, GaN, etc. can be used as the substrate 10. In the following descriptions, the Si is used for the semiconductor substrate 10.

21 denotes a first flow channel in which a sample liquid flows, and 22 denotes a second flow channel in which the sample liquid or an electrolyte flows. The flow channels 21 and 22 are arranged to be partially close to each other in different layouts, and are formed by, for example, etching the silicon substrate 10 in a width of 50 μm and a depth of 2 μm. An upper portion of each of the flow channels 21 and 22 is covered with an insulating thin film (having a thickness of, for example, 200 nm) such as a silicon oxide film ($SiO_2$), a silicon nitride film (SiNx), and an alumina film ($Al_2O_3$). As shown in FIG. 2, the flow channel caps 11 (i.e., lids to seal the flow channels 21 and 22) are formed on the upper portions of the flow channels 21 and 22. Both the first and second flow channels are thereby formed as groove-shaped tunnel flow channels.

41a and 42a denote an inlet and an outlet of the sample liquid, respectively, located at the end of the first flow channel. 41b and 42b denote an inlet and an outlet of the sample liquid or the electrolyte, respectively, located at the end of the second flow channel. 41a, 41b, 42a and 42b are formed by etching a surface portion of the silicon substrate 10 with the depth of 2 μm, for example, with a shape of a 1-mm-sided square, for example. The flow channel caps 11 are formed in the range of the flow channels 21 and 22, and then the inlets and outlets 41a, 41b, 42a, and 42b have no caps. The flow channels 21 and 22 are thereby formed as tunnel-like flow channels opening at the inlets and outlets.

30 is a fine hole provided at a contact portion between the first flow channel 21 and the second flow channel 22. The fine hole 30 is formed by partial etching of a partition 31 (for example, $SiO_2$ wall with a thickness of 0.2 μm) between the flow channels 21 and 22 in a slit shape. A size (width) of the fine hole 30 may be slightly greater than a size of the particles to be detected. When the size of the particles to be detected is 1 μm in diameter, the width of the fine hole 30 in FIG. 1 may be, for example, 1.5 μm.

13a and 13b denote electrodes configured to detect the particles. The electrodes 13a and 13b are formed to be partially exposed inside the flow channels 21 and 22, respectively. As the materials of the electrodes 13a and 13b, AgCl, Pt, Au, etc. may be used in the portion of surfaces where the electrodes are in contact with the sample liquid. The electrodes 13a and 13b are not necessarily be integrated as shown in FIG. 2. Even if external electrodes are attached in the inlets and the outlets of the respective flow channels instead of integrating the electrodes 13a and 13b, the particles can be detected.

An ion current flowing through the fine hole 30 is basically determined based on an aperture size of the fine hole 30. In other words, the static current caused to flow by applying a voltage to the electrodes 13a and 13b which are in the flow channels 21 and 22, respectively, filled with the electrolyte solution is determined based on the aperture size of the fine hole 30.

When a particle passes through the fine hole 30, the particle partially blocks the passage of the ions through fine hole 30, the ion current reduction occurs in accordance with a degree of the blockage. However, if the particle is conductive or can become conductive at a surface level, the ion current increase corresponding to the particle passage thorough the fine hole is observed because of electric conduction of the particle itself caused by giving and receiving ion charges. Such ion current variation is determined based on relative relationships in shape, size, length, etc. between the fine hole 30 and the particles. For this reason, a feature of the particles passing through the fine hole can be recognized by observing the amount of variation, transient variation, etc. of the ion current.

The aperture size of the fine hole 30 may be determined by considering ease of passage of the particles to be detected and variation degree (sensitivity) of the ion current. For example, the aperture size of the fine hole 30 may be 1.5 to 5 times as great as an outer diameter of the particles to be detected. As an electrolyte solution to disperse the particles to be detected, KCl solution or various buffer solutions such as a Tris Ethylene diamine tetra acetic acid (TE) buffer solution and a phosphate buffered saline (PBS) solution can be used.

In the semiconductor micro-analysis chip of the present embodiment shown in FIG. 1 and FIG. 2, for example, the first flow channel 21 is used as a sample liquid flow channel, and the sample liquid (i.e., the suspension liquid obtained by dispersing fine particles to be detected in an electrolyte solution) is dropped to the inlet 41a. At this time, since the flow channel 21 is the tunnel-like flow channel as described above, the sample liquid is sucked into the flow channel 21 by the capillary action, and then an interior of the flow channel 21 is filled with the sample liquid as soon as the sample liquid reaches the entrance of the flow channel 21. The second flow channel 22 is used as a flow channel for receiving the detected particles. The electrolyte solution which does not include the particles to be detected is dropped into the inlet 41b, and then an interior of the flow channel 22 is filled with the electrolyte solution. In above situation, the particles passing through the fine hole 30 can be detected by applying a voltage between the electrodes 13a and 13b.

A polarity of the voltage applied between the electrodes 13a and 13b is different according to charging condition of the particles (bacteria, viruses, labeled particles, etc.) to be detected. For example, to detect negatively charged particles, a negative voltage is applied to the electrode 13a and a positive voltage to the electrode 13b. In this configuration, the particles move and pass through the fine hole by the electric field in the solution, or the particles are electrophoresed, and then the ion current variation is observed according to above mentioned mechanism.

The second flow channel 22 as well as the first flow channel 21 can be filled with the sample liquid. This condition can be employed particularly when the charge of the particles to be detected is unclear or when positively charged particles and negatively charged particles are mixed. Even when the charge of the particles to be detected is known, the detection may be executed by filling both the flow channels with the sample liquid. In this case, because two types of solutions, i.e., the sample liquid and the electrolyte solutions, do not need to be prepared, relevant to detect the particles can be simplified. However, the inlets 41a and 41b (outlets 42a and 42b) of the flow channels need to be electrically separated from each other, i.e., the sample liquid in one of the inlets (outlets) needs to be separated from that in the other one.

Thus, in the semiconductor micro-analysis chip of the present embodiment, the particles can be detected only by the sample liquid introduction and the electric observation. Furthermore, the ultraminiaturization and mass production can be implemented by the semiconductor processing technology, and the particle detection circuit, the particle discrimination circuit, etc. can be integrated. For this reason, ultraminiaturized and high-sensitivity semiconductor micro-analysis chips can be manufactured in large quantity, at low costs. Therefore, using the semiconductor micro-analysis chips of the present embodiment high sensitive detection of bacteria, viruses, etc. can be easily conducted, and the semiconductor micro-analysis chips of the present embodiment can contribute to prevent epidemic diseases to spread and to maintain food safety, by applying the semiconductor micro-analysis chips to rapid test of infectious pathogens, food poisoning-causing bacteria, etc. The semiconductor micro-analysis chips are suitable for the purposes what a large amount of the chips need to be provided at very low costs such as, for example, high-speed primary test kits for diseases which require an emergency quarantine action such as new type influenza, simple food-poisoning tests at ordinary home, etc.

A method of manufacturing the semiconductor micro-analysis chip shown in FIG. 1 and FIG. 2 will be hereinafter described with reference to FIGS. 3A to 3G. The manufacturing process of the typical portions is illustrated in the cross-sectional views.

FIGS. 3A to 3G are the cross-sectional views illustrating the manufacturing process of the semiconductor micro-analysis chip of the present embodiment. Left figures of FIGS. 3A to 3G are the cross-sectional views illustrating the first flow channel 21. Right figures are the cross-sectional views illustrating a contact portion of the first flow channel 21 and the second flow channel 22 as seen along a line intersecting the electrodes 13a and 13b.

In FIG. 3A, 10 denotes a silicon substrate, and 51 denotes an etching mask obtained by patterning a silicon oxide film ($SiO_2$). The $SiO_2$ film 51 is formed by chemical vapor deposition (CVD) with a thickness of 100 nm, for example. Then, the film is patterned by wet etching or dry etching using a resist (not shown) with an aperture pattern formed by photolithography. At this time, the aperture areas of the patterned etching mask 51 are the flow channels 21 and 22, the inlets 41a and 42a, and the slit shaped fine hole which is located at a portion of an isolated pattern 31 at the center in the right figure of FIG. 3A, or the portion 30 in FIG. 1). A width of the partition 31 which separates the first flow channel 21 and the second flow channel 22 at the contact portion of the flow channels from each other (i.e., the isolated pattern at the center in the right figure of FIG. 3A) is set at, for example, 100 nm.

Next, a surface of the silicon substrate 10 is etched in, for example, 2 μm, by using the etching mask 51, as shown in FIG. 3B. The etching of the silicon substrate 10 is executed by deep reactive ion etching (RIE) such as Bosch Process such that the etched side surface is as perpendicular to the substrate 10 as possible.

Next, a thermal oxidized silicon ($SiO_2$) film 11a is formed on a surface of the silicon substrate 10 as shown in FIG. 3C. At this time, the etching mask 51 may be removed prior to thermal oxidation or may be left in a state shown in FIG. 3B. The thermal oxidation is executed by, for example, wet oxidation process to form the $SiO_2$ film with a thickness of, for example, 200 nm. At this time, since the 100 nm-thick partition 31 of the flow channels (i.e., the isolated pattern at the center in the right figure of FIG. 3C) is entirely oxidized from both side surface, the partition 31 becomes a $SiO_2$ fence having a thickness of approximately 230 nm.

Next, the electrodes 13a and 13b are formed as shown in FIG. 3D. The electrodes 13a and 13b may be formed by metal evaporation (resistive heating evaporation, electron beam heating evaporation, spattering, etc.) on an image reverse resist pattern (not shown) and subsequent liftoff process. Alternatively, the electrodes may be formed by etching using the resist pattern, after full-surface metal evaporation. Electrode materials may be Ti/Pt, Ti/Pt/Au, Ti/Pt/AgCl, etc. and, desirably, the materials of the surface in liquid contact are AgCl, Pt, Au, etc.

Figure 3E:
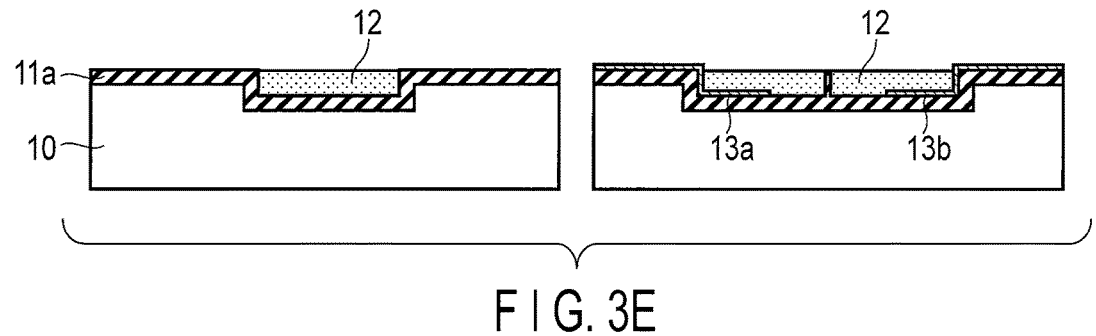

Next, a sacrifice layer 12 to form caps of the flow channels is embedded in the flow channel portions as shown in FIG. 3E. An organic material of polyimide resin, etc. is used as the sacrifice layer 12. For example, a precursor of polyimide resin is spin coated and thermally cured. After that, surfaces of the $SiO_2$ film 11a and portions of the electrodes 13a and 13b on the surface of the substrate are exposed by chemical mechanical polishing (CMP), overall etching of polyimide resin, etc. The material of the sacrifice layer 12 may be a material which can be selectively removed at a final stage and which allows subsequent formation of a layer of an insulating film of $SiO_2$, $SiNx$, $Al_2O_3$, etc., and may not only be an organic material, but the other material.

Figure 3F:
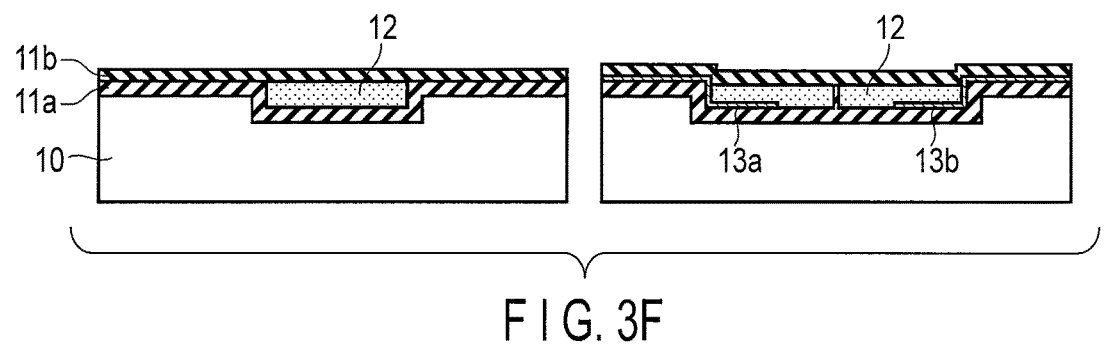

Next, an insulating film ($SiO_2$, $SiNx$, $Al_2O_3$, etc.) which is to be a flow channel cap 11b is formed by CVD, spattering, etc. as shown in FIG. 3F. The insulating film 11b is selectively etched after forming a resist pattern (not shown) having apertures at the inlets (outlets) 41a and 42a (41b and 42b) and an electrode pad (external connection terminal) portion.

Figure 3G:
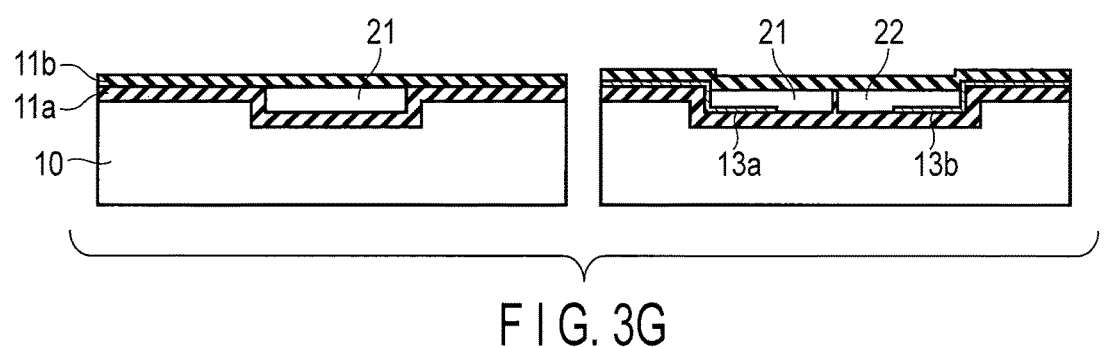

Finally, the sacrifice layer 12 is selectively etched by oxygen plasma ashing, etc. as shown in FIG. 3G. The sacrifice layer 12 in the flow channels is removed via apertures of ends of the flow channels 21 and 22 by oxygen plasma ashing. After removing the sacrifice layer, the flow channels 21 and 22 having upper, lower, right and left sides surrounded by the insulating film are formed.

Thus, the semiconductor micro-analysis chip of the present embodiment can be manufactured in the general semiconductor device manufacturing process using the Si substrate. The particles can be detected at high sensitivity, and fine processing of the semiconductor technology and the mass production technology can be applied to the semiconductor micro-analysis chip. For this reason, the semiconductor micro-analysis chip can be much miniaturized and manufactured at low costs.

(Second Embodiment)

Figure 4:
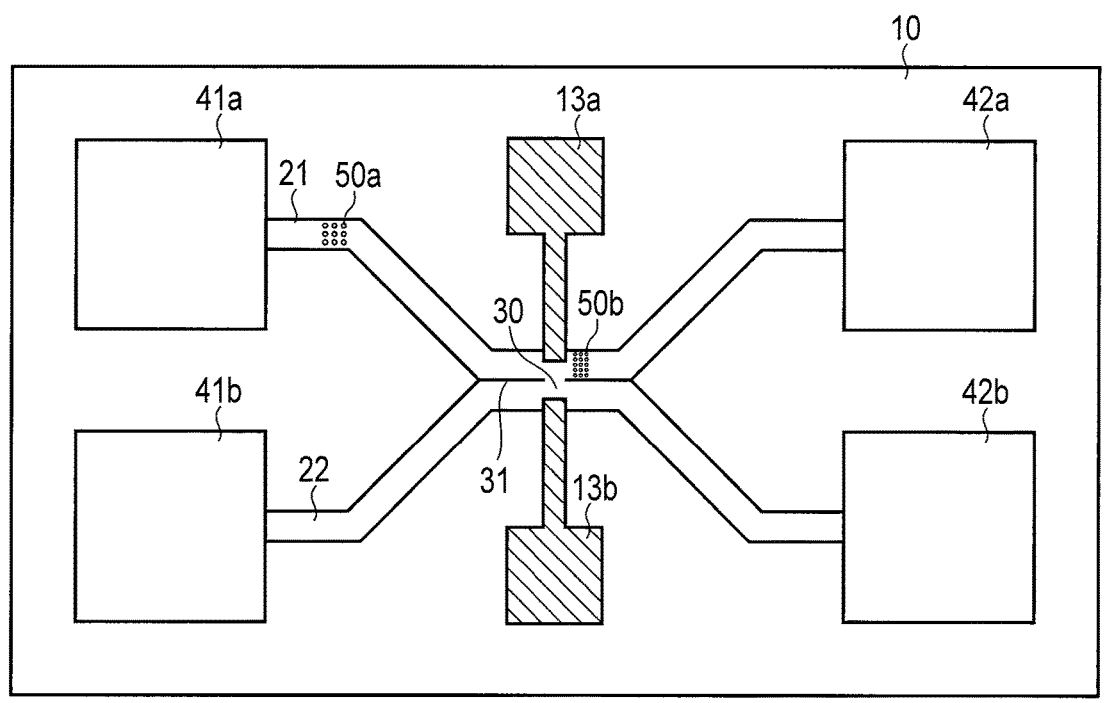
FIG. 4 is a plan view showing a schematic structure of a semiconductor micro-analysis chip of a second embodiment.

FIG. 4 and FIG. 5 illustrate a schematic structure of a semiconductor micro-analysis chip of a second embodiment. FIG. 4 is a plan view and FIG. 5 is a perspective view. In the present embodiment, a particle size filter is provided in a sample liquid flow channel 21.

In FIG. 4 and FIGS. 5, 50a and 50b denote micro-size pillar arrays composed of fine columnar structures (pillars) arranged at regular intervals to filter the particles in the sample liquid by size based on the intervals. Wall-like structures (slit) arrays, etc. can also be used instead of the pillar arrays 50a and 50b. A structure and a function of the particle filter will be described taking the case of introducing the sample liquid to the inlet 41a and guiding the sample liquid to the flow channel 21 for example.

The pattern of pillar arrays (or slit arrays) can be incorporated into an etching mask 51 at the process step of FIG. 3A, and can be formed by providing the mask 51 in the middle of the flow channel 21, at the same time to provide the isolated pattern 31 at the center in the right view of FIG. 3A. Since pillar arrays (or slit arrays) 50 capture the particles in the flowing sample liquid, it is necessary to form no gap between the pillar arrays and a side surface of the flow channel or the flow channel cap, as shown in FIG. 6. In particular, to make no gap between an upper portion of the pillar arrays and the flow channel cap, which cannot be controlled by the mask pattern, it is effective to preliminarily over-etch a surface of the sacrifice layer 12 slightly in the step of FIG. 3E (by, for example, 0.2 µm).

FIG. 7A shows a cross-section of the substrate in a state in which the insulating film 11b is formed after over-etching the sacrifice layer 12 in the step of FIG. 3E. Since the sacrifice layer 12 is over-etched, a partition 31 portion protrudes as compared with the sacrifice layer 12. A top surface of the insulating film (flow channel cap) 11b is therefore uneven at the partition 31 portion. FIG. 7B illustrates the case that the pillar arrays in FIG. 6 are formed. By etching the sacrifice layer 12 to expose the top of pillar arrays, the top surface of the insulating film 11b is uneven above the flow channel 21 comprising the pillar arrays.

Thus, since the partition 31 or the pillar arrays 50 protrude as compared with the top surface of the sacrifice layer 12, the flow channel cap can be certainly formed on the partition 31 or the pillar arrays 50 without gap, and then the flow channel cap and the partition 31 or the pillar arrays 50 are in close contact. When a Si groove serves as the flow channel, formation of the partition or pillars to have the above-described structure is very significant.

Figure 8:
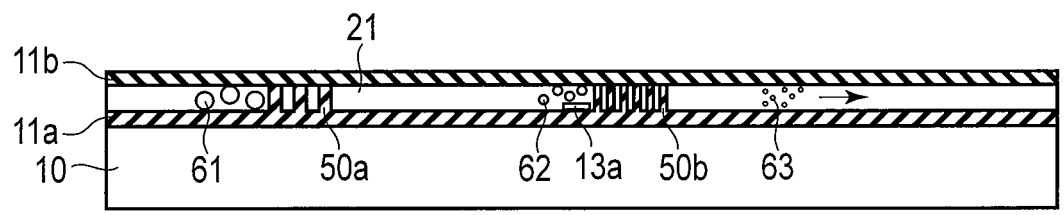
FIG. 8 is a cross-sectional view showing a functional operation of a semiconductor micro-analysis chip of a second embodiment.

FIG. 8 schematically shows a function of pillar arrays 50a and 50b. First pillar arrays 50a are provided at an upstream side of the fine hole 30 and serve as a filter configured to remove large particles 61, which is to clog a fine hole 30. The pillar arrays 50a are formed with intervals which allow the particles to be detected 62 to pass through the pillar arrays 50a but do not allow the particles 61 having a diameter larger than the aperture of the fine hole 30 to pass through. For example, if the size of the particle to be detected is 1 µmφ and the diameter of the fine hole is 1.5 µm, the pillar arrays 50a are arranged in a manner described below. Columnar structures having a diameter of 2 µmφ or quadrangular prism-shaped structures having length of 2 µm on a side are formed so as to have an interval of, for example, 1.3 µm at maximum in the direction of transverse to the flow channel, as the pillar arrays 50a. The number of steps (i.e., number of rows) of the pillar arrays may be determined in consideration of a trap efficiency of the large particles 61. Substantially all particles having an outer diameter of 1.3 µm or more can be trapped providing the pillar arrays in the direction of transverse to the flow channel in, for example, ten steps (ten rows).

In addition, a multi stepped filter structure can be provided such that pillar arrays (not shown) having larger intervals of pillars may be provided in the upstream of the pillar arrays 50a to preliminarily filter the particles having a size of, for example, 5 µmφ or more before the pillar arrays 50a. In this case, the particle filter 50a can easily be prevented itself from being clogged by the large particles 61. For this reason, pretreatments such as centrifugation and preprocessing filtration of the sample liquid can be omitted, and then the work for detecting the particles can be simplified and accelerated.

In FIG. 8, the pillar arrays 50b serve as a collector configured to collect and concentrate the particles to be detected 62, which is provided at a downstream side of the fine hole 30. The pillar arrays 50b are formed with intervals which do not allow the particles to be detected 62 to pass through but allow the electrolyte solution and microparticles 63 which have the size smaller than the size of the particles to be detected 62 to pass through. For example, if the size of the particle to be detected is 1 µmφ, columnar structures having a diameter of 1 µmφ or quadrangular prism-shaped structures having a length of 1 µm on a side are formed so as to have an interval of, for example, 0.9 µm at maximum in the direction of transverse to the flow channel, as the pillar arrays 50b. The number of steps (i.e., number of rows) of the pillar arrays may be determined in consideration of a trap efficiency of the particles to be detected 62. Substantially all particles having an outer diameter of 1.0 µm or more can be trapped by providing the pillar arrays in the direction of transverse to the flow channel 21 in, for example, ten steps (ten rows).

Figure 9A:
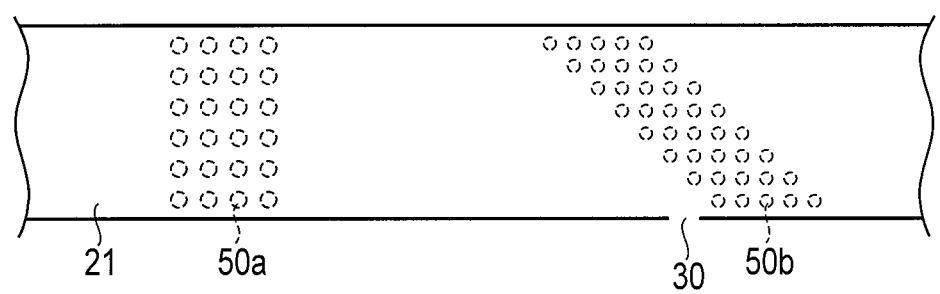
FIGS. 9A and 9B are illustrations showing a modified example of the second embodiment.
Figure 9B:
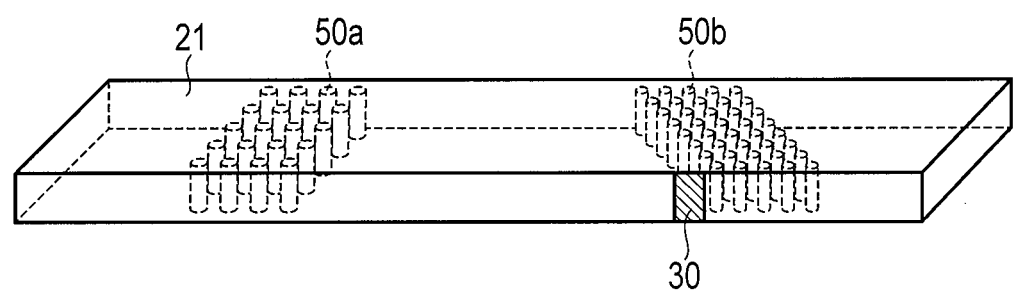

In addition, the pillar arrays 50b may be aligned so as to obliquely intersect the flow channel 21, with the fine hole 30 positioned in vicinity of a portion located at the most downstream side of the upstream side end of the pillars, as shown in FIGS. 9A and 9B. Since the trapped particles are guided to the portion of the fine hole 30 with a good efficiency, the detection efficiency can be enhanced.

Not only the case that both the pillar arrays 50a and 50b are provided, but the case either the pillar arrays 50a or the pillar arrays 50b are provided may be possible. These can be decided in consideration of features of the sample liquid to be applied, process of detection steps, etc. In addition to the pillar arrays 50a and 50b which serve as particle size filters, pillar arrays with intervals greater than the intervals of the pillar arrays 50a and 50b may be formed all over the flow channel. In this case, each of the pillars can function as a supporting column of the cap of the flow channel and can prevent the flow channel cap from being collapsed by an outer pressure or a surface tension of the sample liquid. Furthermore, the surface tension of the electrolyte solution can also act between the pillars, which work as a driving force to suck the electrolyte solution, resulting in further ease in filling the flow channel with the sample liquid and the electrolyte solution.

Pillar arrays may also be formed with intervals greater than the pillar intervals which can be the particle size filter, in the regions of the sample liquid inlets 41a and 41b and the sample liquid outlets 42*a* and 42*b*. With above configuration, the sample liquid and the electrolyte solution dropped onto the inlets can be spread by the surface tension of the pillar arrays and the solutions can smoothly flow into the flow channel.

Thus, in the present embodiment, the particle size filtering function can be added by arranging the pillar arrays (or slit arrays) in the sample liquid inlet flow channel. Furthermore, the detection steps can be simplified and the accuracy in detection of the particles can be enhanced by adding functions of removing unnecessary particles, concentrating the particles to be detected, etc. Therefore, the detection time can be reduced and the detection errors can be reduced and prevented.

(Third Embodiment)

FIG. 10 is a perspective view showing a schematic structure of a semiconductor micro-analysis chip of a third embodiment. In this embodiment, flow channels 21 and 22 are not constituted by grooves of a silicon substrate 10, but covered with tunnel-like insulating films.

In the embodiments shown in FIG. 2 and FIG. 5, the steps of forming the grooves of the flow channels 21 and 22 and selectively filling the grooves with a sacrifice layer 12 is necessary (FIG. 3E). In the method of etching back the entire surface of the sacrifice layer 12, however, the etching rate of the sacrifice layer is remarkably varied between the regions where the grooves are formed and not. For this reason, stopping the etching is difficult in the state shown in FIG. 3E. In addition, etching failure such as residue of the sacrifice layer outside the grooves, and excessive etching of the sacrifice layer at the grooves may easily occur due to variation in etching in the wafer surface. On the other hand, if the sacrifice layer is embedded in the grooves using CMP, the sacrifice layer residue may easily occur at stepped portions of the electrodes 13 and 13*b*. Above-mentioned situations often result in not only process failure such as peeling of films subsequently formed, but also leak failure of an ion current in a gap of the insulating films.

Accordingly, in the present embodiment, hollow structure with walls and ceilings formed with insulating films on the silicon substrate 10 are used as the flow channels instead of the grooves on the silicon substrate 10. In other words, forming the sacrifice layer 12 in the flow channel pattern, covering a top surface and side surfaces of the sacrifice layer 12 by an insulating film, and removing the sacrifice layer 12, flow channels of an insulating film tunnel type are formed. FIGS. 11A to 11F shows the manufacturing steps.

FIGS. 11A to 11F are cross-sectional views illustrating the manufacturing process of a semiconductor micro-analysis chip of the present embodiment. In each drawing, a left side illustrates a cross-section of a pillar array formation portion of a first flow channel 21 and a right side illustrates a cross-section of a second flow channel 22. A partition 31 at a contact portion of the flow channels 21 and 22 is formed similarly to that illustrated in the right views of FIGS. 3A to 3G, and their descriptions are omitted. In addition, since electrodes 13*a* and 13*b* are formed similarly as well, their descriptions are also omitted.

In FIG. 11A, 10 denotes a silicon substrate, and 51 denotes an etching mask obtained by forming a SiO$_2$ film having a thickness of 100 nm by CVD and patterning the film using photolithography.

A surface of the silicon substrate 10 is etched in the depth of, for example, 2 µm, by RIE using the etching mask 51 as a mask, as shown in FIG. 11B. At this time, apertures of the etching mask 51 are region for flow channels, reservoir portions and a fine hole, but the cross-sectional width of the region for flow channel is set to L sufficiently greater than a final flow channel width. L is set to include the width of two flow channels and to sufficiently include the outer portions of the flow channels. In addition, pillar arrays 50 are also formed in this step. By forming the pillar arrays 50 in a region wider than the flow channel width, occurrence of a gap caused by pattern deviation between the pillar arrays and the flow channels can be prevented.

Next, a thermal oxide SiO$_2$ film 11*a* is formed on a surface of the silicon substrate 10 as shown in FIG. 11C. At this time, the etching mask 51 may be removed prior to thermal oxidation or may be left as it is. The thermal oxidation is executed by, for example, wet oxidation such that the SiO$_2$ film has a thickness of 200 nm. The entire body of the pillar arrays 50 becomes a SiO$_2$ film by the thermal oxidation.

Next, electrodes 13*a* and 13*b* (not shown) are formed and a sacrifice layer 12 which is to form flow channel walls and ceilings is formed in a flow channel pattern as shown in FIG. 11D. Using photosensitive polyimide resin as the sacrifice layer 12, the sacrifice layer pattern can be directly formed by applying, exposing and developing the resin.

Next, an insulating film 11*b* (SiO$_2$, SiNx, Al$_2$O$_3$, etc.) which is to serve as the flow channel walls and caps is formed to have a thickness of, for example, 500 nm, by CVD or spattering as shown in FIG. 11E. Then, apertures are formed in the insulating film 11*b* at reservoir portions and electrode pad portions.

Finally, the sacrifice layer 12 is selectively removed by oxygen plasma ashing, etc. as shown in FIG. 11F. The sacrifice layer 12 is ashed and removed from apertures of end portions of the flow channels 21 and 22 by oxygen plasma. The flow channels 21 and 22 having upper, lower, left and right portions surrounded by the insulating films are formed by removing the sacrifice layer 12.

Since the present embodiment does not include etch-back process or CMP process of the sacrifice layer 12, in-plane unevenness such as residue of the sacrifice layer 12 and reduction of film thickness hardly occurs. Process failure in the sacrifice layer formation steps is therefore remarkably reduced. In addition, since a gap between the thermal oxide film 11*a* and the cap film 11*b* which would be caused by the residue of the sacrifice layer hardly occurs essentially, leak failure of the ion current is also solved substantially.

The reservoirs (41*a*, 41*b*, 42*a* and 42*b*) of the present embodiment can be basically formed similarly to those shown in FIG. 2 and FIG. 5, but liquid dams of the reservoirs need to be formed at portions of connection between the flow channels of the insulating film type and the reservoirs. For this reason, Si terraces may be formed beside the apertures at the ends of the flow channels 21 and 22 as shown in FIG. 10. In addition, dummy flow channels may be formed at up to Si terrace portions, beside the apertures at the ends of the flow channels, and may be used as liquid dams.

(Fourth Embodiment)

FIG. 12 is a plan view showing a schematic structure of a semiconductor micro-analysis chip of a fourth embodiment. In the present embodiment, a flow channel 21 and a flow channel 22 are formed in different steps, and a piled portion (contact portion) where the two flow channels intersect each other is provided, i.e., double-decker flow channels in which the flow channel 21 serving as a sample supplying flow channel is formed at a lower side and the flow channel 22 serving as a sample receiving flow channel is formed at an upper side are provided. At this time, a fine hole 30 is provided at the piled portion (contact portion) of the two flow channels. In other words, the fine hole 30 is formed by photolithography, at a partition (i.e., a cap insulating film of a first flow channel) which serves as an upper surface of a first flow channel 21 and a lower surface of a second flow channel 22.

In the embodiments shown in FIG. 1 to FIG. 11, the fine hole 30 needs to be formed at the partition perpendicular to the silicon substrate 10 since two flow channels are laterally adjacent to each other with the partition sandwiched between them. For this reason, the slit-like fine hole 30 is formed by patterning the partition from the side portions. At this time, the shape of the fine hole is a rectangle similar to a square when a depth of the flow channels is the same as a width of the fine hole, otherwise a vertically long slit when the depth of the flow channels is greater than the width of the fine hole. For this reason, when the particles pass through the fine hole 30, the aperture of the fine hole 30 cannot be sufficiently shielded by the particles, and then the variation in an ion current is small as compared with a circular fine hole.

In the embodiment shown in FIG. 12, however, the fine hole 30 can be directly patterned and the aperture shape of the fine hole can be arbitrarily determined. For this reason, the fine hole 30 can be designed to have a circular aperture by which the ion conduction can be most effectively shielded with the particles. At this time, the variation in the ion current associated with the passing of particles to be detected through the fine hole 30 can be maximized and the particles can be detected with much higher sensitivity than the detection in the embodiments shown in FIG. 1 to FIG. 11.

Figure 13:
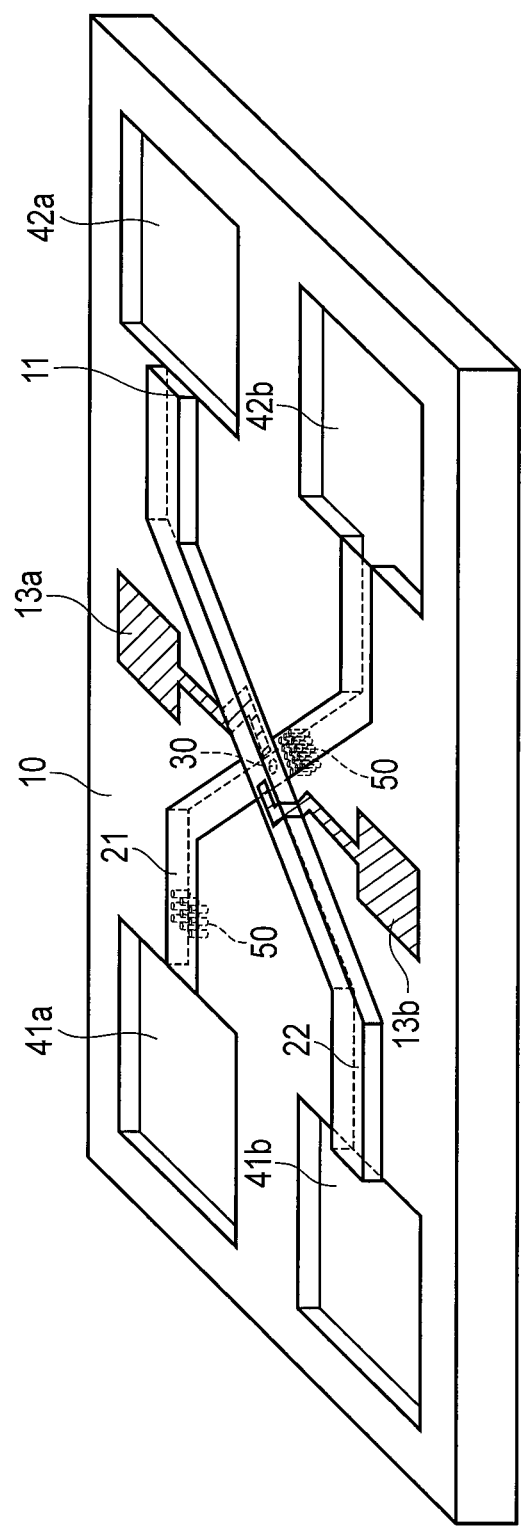
FIG. 13 is a perspective view showing the schematic structure of the semiconductor micro-analysis chip of the fourth embodiment.

FIG. 13 shows a concrete example of the double-decked flow channels. In this example, the first flow channel 21 is a tunnel flow channel of a Si substrate engraving type similarly to the flow channel shown in FIG. 2 while the second flow channel 22 is a flow channel of an insulating film tunnel type similarly to the flow channel shown in FIG. 8. The first flow channel 21 is formed in the same manner as the steps shown in FIGS. 3A to 3G, and the second flow channel 22 is formed in the same manner as the steps shown in FIGS. 11A to 11F excluding the engraving step of the silicon substrate 10. However, the formation of the first flow channel 21 is executed until the step shown in FIG. 3F. After that, the fine hole 30 is formed at a flow channel contact portion of an insulating film 11b.

Subsequently, the second flow channel 22 is formed in the steps shown in FIGS. 11D to 11F, and the sacrifice layer 12 of the first flow channel 21 and of the second flow channel 22 are entirely removed simultaneously in the step shown in FIG. 11F. An electrode 13a is formed in the step shown in FIG. 3D., and an electrode 13b can be positioned on an upper surface of the second flow channel 22 if the electrode 13b is formed immediately after the step shown in FIG. 11D.

Figure 14A:
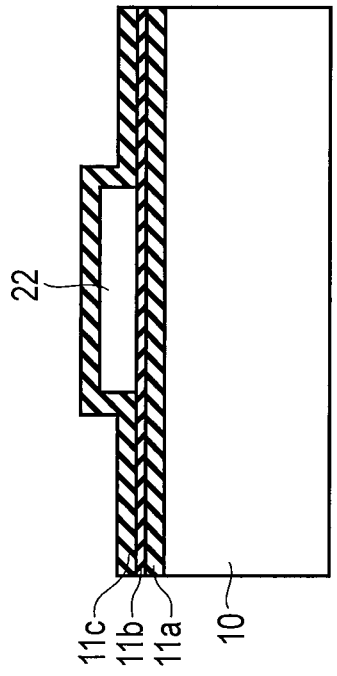
FIGS. 14A to 14C are cross-sectional views showing the schematic structure of the semiconductor micro-analysis chip of the fourth embodiment.
Figure 14B:
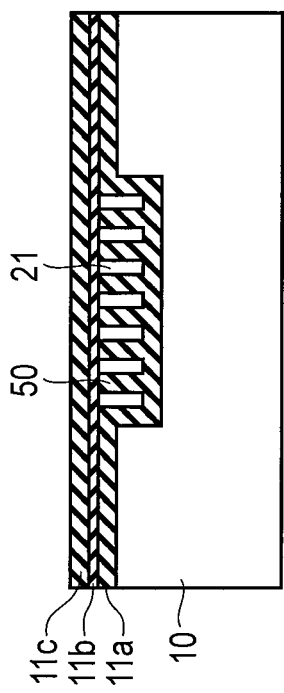
Figure 14C:
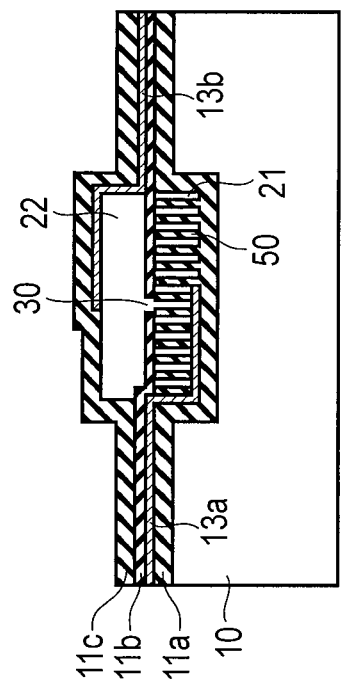

As a result, the first flow channel 21 is a tunnel flow channel of an engraving type as shown in FIG. 14A and the second flow channel 22 is a flow channel of an insulating film tunnel type as shown in FIG. 14B. In addition, the fine hole 30 is formed in the insulating film 11b, at the contact portion where the two flow channels intersect each other, as shown in FIG. 14C, and an aperture shape of the fine hole can be determined arbitrarily. The electrodes for observing the ion current are formed on a lower surface of the first flow channel 21 and an upper surface of the second flow channel 22. High sensitivity can be thereby obtained by optimizing the shape of the fine hole while inheriting the advantages of the above-described embodiments. In addition, the present embodiment comprises the tunnel flow channel of the Si engraving type, and the second flow channel 22 is formed on the insulating film 11b. The present embodiment therefore also has an advantage that even if a gap is generated between the insulating films 11a and 11b due to the residue of the sacrifice layer, a leak current is not generated between the two flow channels.

In the present embodiment, the sample liquid introduced in the inlet 41a is discharged into the outlet 42b since the two flow channels are arranged to intersect each other. However, the arrangement of the two flow channels is not limited to the intersection. For example, the two flow channels may be arranged as shown in a plan view of FIG. 15 or a perspective view of FIG. 16. In other words, the two flow channels may be arranged to be stacked and then to return to the respective own flow channel sides (i.e., the sample liquid introduced in the inlet 41a may be discharged into the outlet 42a).

Figure 17A:
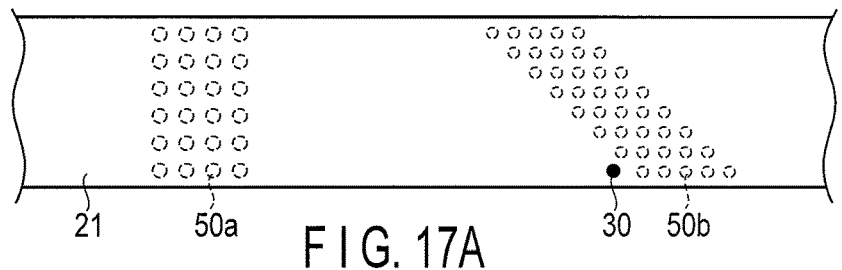
FIGS. 17A to 17D are illustrations showing a modified example of the fourth embodiment.
Figure 17B:
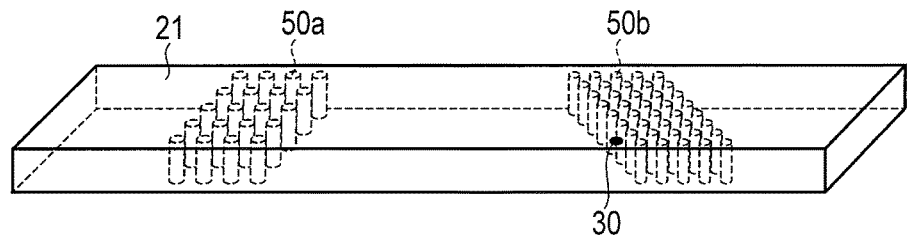

In FIGS. 17A and 17B, pillar arrays 50b are arranged such that pillars obliquely cross the flow channel 21, and that the fine hole 30 is positioned near a portion at the most downstream side, of the pillars of the upstream side. FIG. 17A is a plan view and FIG. 17B is a perspective view. Thus, a detection efficiency can be enhanced since the particles trapped by the pillar arrays 50b are guided to the fine hole 30 with a good efficiency.

Figure 17C:
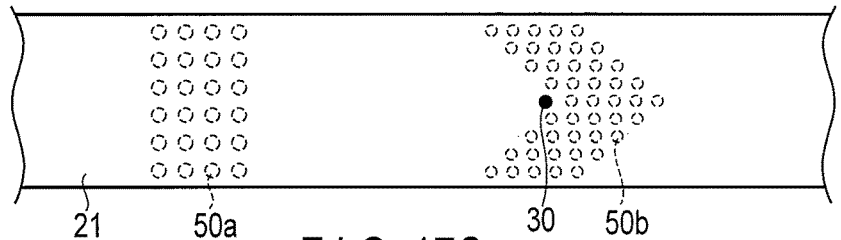
Figure 17D:
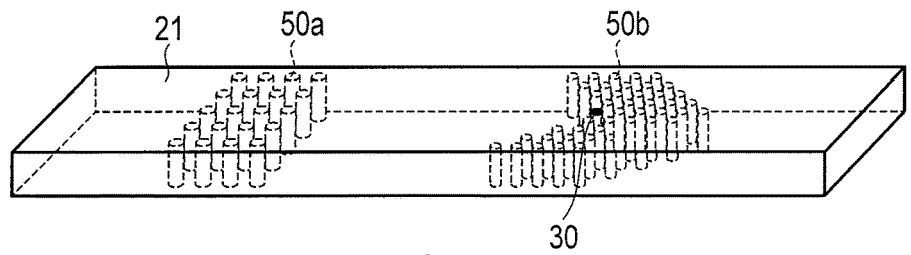

Furthermore, In FIGS. 17C and 17D, the pillar arrays 50b are arranged in a form ">" about the flow channel direction. FIG. 17C is a plan view and FIG. 17D is a perspective view. The same advantage as that of the arrangement shown in FIG. 17A and FIG. 17B can also be obtained from the arrangement of the pillar arrays. Considering the case that the fine hole 30 is formed in a predetermined size, the fine hole 30 is positioned at a central portion of the flow channel 21, in the arrangement of the form ">". For this reason, the arrangement of the form ">" shown in FIG. 17C and FIG. 17D can be formed more easily than the "oblique" arrangement shown in FIG. 17A and FIG. 17B.

Figure 18:
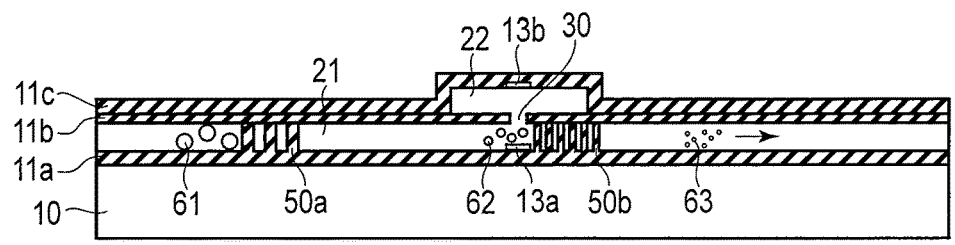
FIG. 18 is a cross-sectional view showing the schematic structure of the semiconductor micro-analysis chip of the fourth embodiment.

FIG. 18 schematically shows a particle detecting mechanism of the present embodiment. A function of the pillar arrays 50a and 50b is the same as that in FIG. 8. In FIG. 18, applying a voltage between the electrodes 13a and 13b, the particles 62 collected by the pillar arrays 50b are electrophoresed between the electrodes 13a and 13b and moved to the flow channel 22 side through the fine hole 30. At this time, since the ion current flowing between the electrodes 13a and 13b varies, the particles 62 can be detected.

According to the present embodiment, since the fine hole 30 is formed to have the circular aperture by stacking the first flow channel 21 and the second flow channel 22, not only the same advantages as those of the first embodiment can be obtained, but also the particles can be detected with a higher sensitivity.

(Fifth Embodiment)

FIG. 19 is a perspective view showing a schematic structure of a semiconductor micro-analysis chip of a fifth embodiment. The present embodiment is a modification case in which a flow channel 21 and a flow channel 22 are formed in different steps and a piled portion (contact portion) of the two flow channels is provided.

Both the first flow channel 21 which is a sample inlet flow channel and the second flow channel 22 which is a sample receiving flow channel are insulating film tunnel type flow channels. The two flow channels are formed in different steps, and a fine hole 30 is formed by photolithography, at the piled portion of the two flow channels.

The present embodiment is characterized by solving inconvenience that filling the second flow channel with a sample liquid or an electrolyte solution sometimes cannot be successfully executed for the reason that the second flow channel 22 is different in height from the reservoir connection portion (aperture portion) in the embodiment shown in FIG. 13. In the present embodiment, the first flow channel 21 of an insulating film tunnel type is formed in a flow channel portion 10a formed on a substrate, and the second flow channel 22 of an insulating film tunnel type, is formed in the same steps as the first flow channel 21, after the formation of the first flow channel 21. The first flow channel 21 and the second flow channel 22 can be thereby substantially the same height at their reservoir portions.

Figure 22:
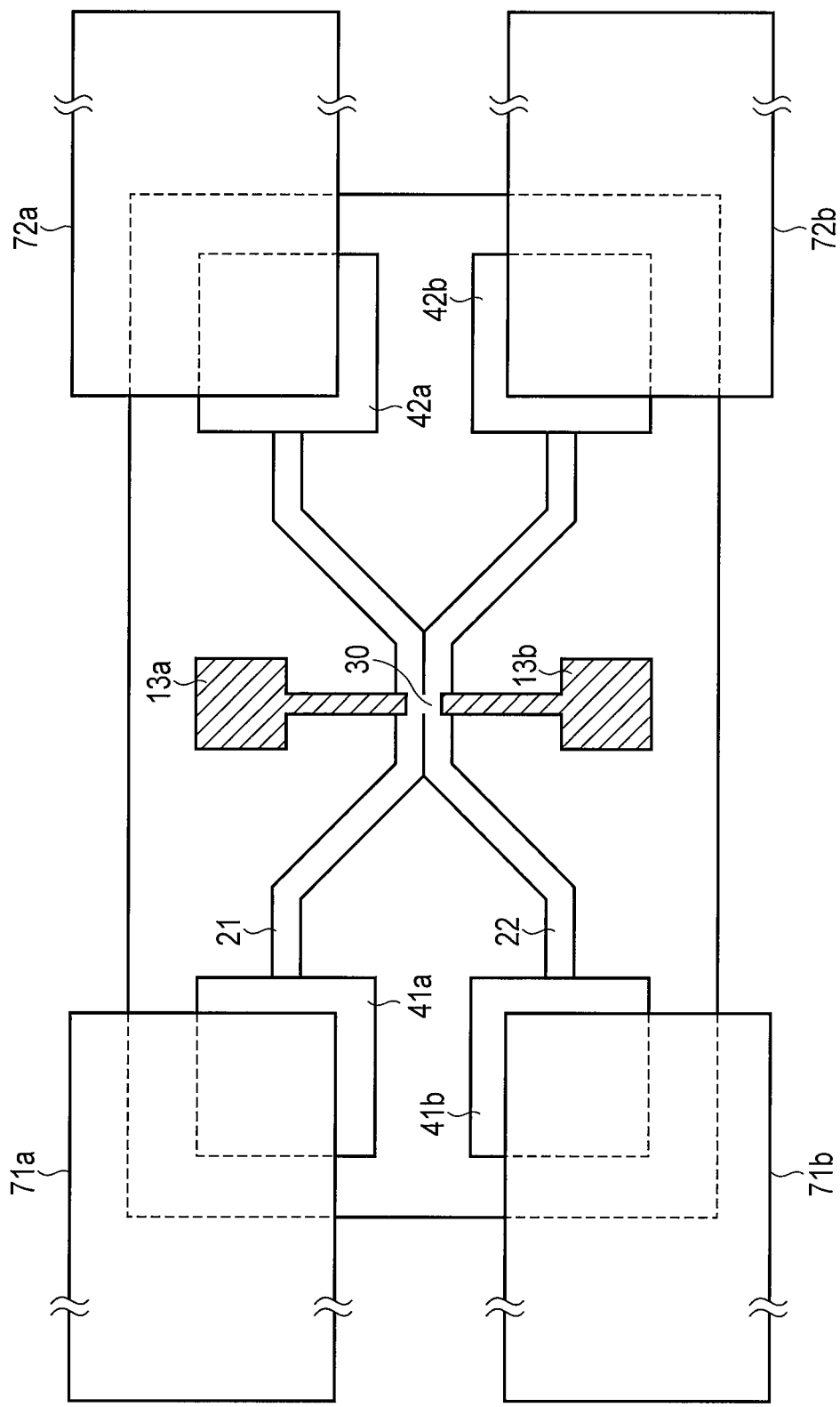
FIG. 22 is a plan view showing a schematic structure of a semiconductor micro-analysis chip of a seventh embodiment.

At the piled portion (i.e., contact portion in FIG. 19) of the two flow channels, a space of the second flow channel 22 can be secured as shown in FIG. 22, because, in the process forming the second flow channel, a sacrifice layer for the second flow channel automatically climbs over the first flow channel 21. In the case of filling the first flow channel 21 and the second flow channel 22 with the sample liquid (or electrolyte solution), a problem that filling failure occurs at either of the flow channels can be thereby solved.

Thus, the present embodiment has an advantage that failure in filling the flow channels with the sample liquid or the electrolyte solution can be solved, besides the advantage of the fourth embodiment.

(Sixth Embodiment)

FIG. 20 is a perspective view showing a schematic structure of a semiconductor micro-analysis chip of a sixth embodiment. The present embodiment is a modification case in which a flow channel 21 and a flow channel 22 are formed in different steps and providing a piled portion (contact portion) of the two flow channels. FIG. 21A is a cross-sectional view of the flow channels and FIG. 21B is a cross-sectional view of the contact portion of the flow channels.

Similarly to the embodiment shown in FIG. 19, both the first flow channel 21 which is a sample inlet flow channel and the second flow channel 22 which is a sample receiving flow channel are insulating film tunnel type flow channels. The two flow channels are formed in different steps, and a fine hole 30 is formed by photolithography, at the piled portion of the two flow channels. Furthermore, the second flow channel 22 is formed to be higher than the first flow channel 21, as shown in FIG. 21A and FIG. 21B.

A space above the first flow channel 21, which works as the second flow channel 22, can be certainly secured at the piled portion (contact portion) of the flow channels 21 and 22. A problem that the second flow channel 22 is crushed at the piled portion of the flow channels 21 and 22, which may often arise in the embodiment shown in FIG. 19, can be therefore solved. In the embodiment shown in FIG. 19, the second flow channel 22 is formed in expectation that a second sacrifice layer would naturally climb over the first flow channel 21. However, because of product variations of the sacrifice layer materials and fluctuations of the temperature or moisture in the processing environment, it is difficult to form the flow channels in certain reproducibility. In the embodiment shown in FIG. 20, the expectation that a top surface of the second flow channel naturally climbs over the first flow channel is not needed, because the flow channels which have different height can be certainly formed by different conditions for coating the sacrifice layer (i.e., spin speed, etc.) or using the sacrifice layer materials of different viscosity.

At this time, it is desirable that the first flow channel 21 and the second flow channel 22 are formed to have the same cross-sectional area to equalize the amounts of filling of the sample liquid (or electrolyte solution) in the flow channels 21 and 22, which cause the capillary action substantially equally in the flow channels 21 and 22. For example, in the case that the first flow channel 21 has a width of 50 µm and a height of 2 µm and the second flow channel 22 has a width of 20 µm and a height of 5 µm, the flow channels 21 and 22 have the same cross-sectional area and the 3 µm-height space between the first flow channel and the second flow channel can be secured at the piled portion.

The present embodiment therefore has an advantage that the problem of crushing the piled portion of the flow channels 21 and 22 can be solved and the micro-analysis chip of higher reliability can be implemented, besides the advantage of the fifth embodiment.

(Seventh Embodiment)

FIG. 22 is a plan view showing a schematic structure of a semiconductor micro-analysis chip of a seventh embodiment. In the present embodiment, a sample liquid is introduced into both a flow channel 21 and a flow channel 22, but an electrolyte solution may be introduced into either of the flow channels instead of the sample liquid.

An absorber 71a which can absorb the sample liquid is arranged on a reservoir 41a and an absorber 71b which can absorb the sample liquid or an electrolyte solution is arranged on a reservoir 41b. Furthermore, an absorber 72a which can absorb the sample liquid is arranged on a reservoir 42a and an absorber 72b which can absorb the sample liquid or the electrolyte solution is arranged on a reservoir 42b. As the absorbers, filter papers and fiber assemblies such as unwoven fabric can be used. Each of the absorbers may be arranged to cover over a corresponding reservoir or arranged to partially cover the corresponding reservoir. However, the absorbers of adjacent reservoirs need to be separated from each other.

As described above in the first embodiment, the sample liquid is supplied to the reservoir 41a and any one of the sample liquid and the electrolyte solution may be supplied to the reservoir 41b. An example of supplying the sample liquid to the reservoir 41b will be hereinafter described.

In this structure, the sample liquid including particles to be detected dropped on the absorbers 71a and 71b seeps from the absorbers 71a and 71b and is guided into the reservoirs 41a and 41b. The sample liquid guided into the reservoirs 41a and 41b reach the reservoirs 42a and 42b through the flow channels 21 and 22, respectively. The sample liquid flowing through the flow channels 21 and 22 is absorbed into the absorbers 72a and 72b arranged on the reservoirs 42a and 42b. Once the absorbers 72a and 72b start absorbing the sample liquid in the reservoirs 42a and 42b, subsequent sample liquid flowing into reservoirs 42a and 42b is absorbed into the absorbers 72a and 72b. Thus, the sample liquid in the flow channels 21 and 22 flows continuously.

In other words, by absorbing the sample liquid using the absorbers 72a and 72b, the sample liquid in the flow channels 21 and 22 can be made to flow without using electrophoresis or an external pump, and the particles included in the sample liquid can be made to move in the flow of the sample liquid. For this reason, the absorbers 71a and 71b on the sides of the reservoirs 41a and 41b can be omitted.

In addition, a sufficient amount of the sample liquid can be supplied into the flow channels 21 and 22 without increasing the size of the semiconductor micro-analysis chip, by arranging the absorbers 71a and 71b on the sample liquid inlet side. In general, introduction of the sample liquid into a micro-analysis chip is executed by using a micropipet, etc. and the amount of instillation of the sample liquid is approximately 10 to 10,000 µl. To contain this amount of the sample liquid, for example, an area of approximately 100 mm² is required with a depth of 100 μm. To integrate such a large containing region results in the semiconductor micro-analysis chip, whose size is remarkably larger than a size required for integrating a functional part of an analysis chip, which causes manufacturing costs to be remarkably increased. In addition, concentration of the particles in the sample liquid is generally low. If it is necessary to detect a number of fine particles, a large amount of sample liquid needs to be introduced into the chip, and then the sample liquid containing region nees to be vast.

In the semiconductor micro-analysis chip of the present embodiment, sufficiently large absorbers 71a and 71b are provided outside the analysis chip, instead of integrating a very large sample liquid containing portion. Then, the sample liquid is instilled into the absorbers 71a and 71b and introduced into the flow channels 21 and 22. The sample liquid discharged from a sample outlet side can be absorbed into the absorbers 72a and 72b. Thus, a larger amount of sample liquid than the amount of the sample liquid contained in the analysis chip can be introduced and discharged.

It is desirable that pillar arrays with intervals greater than that of the above-mentioned particle size filter are formed in regions of the reservoirs 41a, 41b, 42a and 42b and that the absorbers are arranged to contact the pillar arrays. Thus, delivery of the sample liquid or the electrolyte solution between the absorbers 71a, 71b, 72a and 72b and the corresponding reservoirs is smoothly executed by a surface tension of the pillar arrays. Furthermore, the sample liquid or the electrolyte solution can easily and smoothly be introduced from the absorbers into a flow channel.

Thus, according to the present embodiment, the following advantages can be obtained, besides the same advantages as the first embodiment, by providing the absorbers 71a, 71b, 72a and 72b on the reservoirs 41a, 41b, 42a and 42b.

In other words, the sample liquid in the flow channels 21 and 22 can be made to flow without using electrophoresis or an external pump, by providing the absorbers 72a and 72b on sides of sample liquid outlets 42a and 42b. Furthermore, a sufficient amount of the sample liquid can be supplied to the flow channels 21 and 22 without increasing the size of the semiconductor micro-analysis chip, by providing the absorbers 71a and 71b on sides of sample liquid inlets 41a and 41b. A large amount of sample liquid can be therefore handled by the analysis chip of a very small size. In other words, costs can be remarkably reduced by integrating functional portions of the semiconductor micro-analysis chip in a minimum area.

(Eighth Embodiment)

FIG. 23 and FIG. 24 show a schematic structure of a semiconductor micro-analysis chip of an eighth embodiment. FIG. 23 is a plan view and FIG. 24 is a perspective view.

In the present embodiment, a sample liquid inlet port 81 is provided on a package 80 configured to contain the semiconductor micro-analysis chip shown in FIG. 22. The sample liquid inlet port 81 is formed by forming an aperture on a top surface located above absorbers 71a and 71b of the package 80 and providing a funnel-like solution guide configured to guide a sample liquid to the absorbers 71a and 71b. The sample liquid inlet port 81 is great enough to spread over both the absorbers 71a and 71b. A partition plate 82 configured to separate the sample liquid in the absorbers 71a and 71b is provided at the sample liquid inlet port 81.

FIG. 23 does not illustrate absorbers 72a and 72b on a sample liquid outlet side but, of course, the absorbers 72a and 72b may be provided. In addition, a structure of a semiconductor micro-analysis chip 90 is not limited to an example shown in FIG. 22, but can be arbitrarily modified similarly to the above-described embodiments.

In this structure, the sample liquid can be absorbed into the absorbers 71a and 71b with certain separation, only by dripping the sample liquid onto a central portion of the sample liquid inlet port 81. Then, the sample liquid can be guided to reservoirs 41a and 42b corresponding to the absorbers 71a and 71b, respectively, and can be made to further flow into flow channels 21 and 22. Therefore, the sample liquid does not need to be introduced to the reservoirs 41a and 42b independently, and can be guided by a simple operation. In addition, the size of the micro-analysis chip, particularly, the size of the reservoir portions can be minimized enough to overlap the absorbers, and the micro-analysis chip can be ultra-miniaturized. As a result, costs for the micro-analysis chip can be lowered.

(Modified Embodiments)

The semiconductor micro-analysis chip is not limited to the above-described embodiments.

The Si substrate is mainly used in the embodiments. The material of the substrate is not limited to Si, but the other semiconductor substrate materials can be used if the semiconductor substrate can be processed in a general semiconductor manufacturing process. In addition, the insulating film is mainly expressed as dielectric ($SiO_2$, SiNx, $Al_2O_3$), but a type, a composition, etc. of the film can be arbitrarily selected. Otherwise, for example, an organic insulating film can also be used.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A semiconductor micro-analysis chip for detecting particles in a sample liquid, the chip comprising:
   a semiconductor substrate;
   a first flow channel which has walls, a top surface, and a bottom surface, and which is provided on the semiconductor substrate, and through which the sample liquid or an electrolyte solution passes, a first outlet of the sample liquid or the electrolyte solution being provided at one end side of the first flow channel, and a first inlet of the sample liquid or the electrolyte solution being provided at the other end side of the first flow channel;
   a second flow channel which has walls, a top surface, and a bottom surface, and which is provided at a different position from the first flow channel of the semiconductor substrate, and through which the sample liquid or the electrolyte solution passes, a second outlet of the sample liquid or the electrolyte solution being provided at one end side of the second flow channel, and a second inlet of the sample liquid or the electrolyte solution being provided at the other end side of the second flow channel, wherein a portion of the second flow channel intersecting with a portion of the first flow channel overlaps the portion of the first flow channel such that an entirety of the portion of the first flow channel passes underneath the portion of the second flow channel, the portion of the second flow channel being in contact with the portion of the first flow channel with a partition interposed therebetween, and at least a portion of the partition being the top surface of the first flow channel and the bottom surface of the second flow channel;

a fine hole which is provided in the partition and through which the particles pass;

a first electrode exposed at least in part in the first flow channel; and a second electrode exposed at least in part in the second flow channel, wherein the first electrode and the second electrode face each other across the fine hole.

2. The chip of claim 1, further comprising: a particle size filter arranged in one of the first flow channel and the second flow channel, the particles passing through or being collected by the particle size filter.

3. The chip of claim 1, wherein:
the first flow channel is a groove-shaped tunnel-like flow channel comprising a groove provided in the semiconductor substrate,
the second flow channel is a stack-shaped tunnel-like flow channel which forms a hollow structure provided on the semiconductor substrate.

4. The chip of claim 1, wherein:
each of the first flow channel and the second flow channel is a stack-shaped tunnel- like flow channel which forms a hollow structure provided on the semiconductor substrate.

5. The chip of claim 4, wherein at portions of the first and second flow channels other than the intersecting portions of the first and second flow channels, the bottom surface of the second flow channel is higher than the bottom surface of the first flow channel, and the top surface of the second flow channel is higher than the top surface of the first flow channel.

6. The chip of claim 1, further comprising a particle size filter arranged at a downstream side of the fine hole in one of the first flow channel and the second flow channel, the particles being collected by the particle size filter while the sample liquid passes therethrough,
wherein the particles pass through the fine hole from the flow channel on a side where the particle size filter is provided to the other flow channel.

7. The chip of claim 6, wherein:
the particle size filter comprises microscopic columnar structures arranged at regular intervals, and
the columnar structures are arranged to cross obliquely to the flow channel.

8. The chip of claim 1, wherein the chip further comprises a first absorber which absorbs the sample liquid or the electrolyte solution on the first outlet, and a second absorber which absorbs the sample liquid or the electrolyte solution on the second outlet.

9. The chip of claim 8, wherein the chip further comprises a third absorber which absorbs the sample liquid or the electrolyte solution on the first inlet, and a fourth absorber which absorbs the sample liquid or the electrolyte solution on the second inlet.

10. The chip of claim 8, wherein each of the first and second outlets is a groove-shaped outlet provided in the semiconductor substrate, a plurality of columnar structures are provided on each of the first and second outlets, and each of the first absorber and the second absorber is provided on corresponding columnar structures of the plurality of columnar structures and the substrate.

11. The chip of claim 1, wherein the chip further comprises a first absorber which absorbs the sample liquid or the electrolyte solution on the first inlet, and a second absorber which absorbs the sample liquid or the electrolyte solution on the second inlet.

12. The chip of claim 1, wherein:
each of the first flow channel and the second flow channel is a stack-shaped tunnel-like flow channel which forms a hollow structure provided on the semiconductor substrate, and a width of the second flow channel is narrower than a width of the first flow channel.

13. The chip of claim 1, wherein the portion of the first flow channel is a middle portion of the first flow channel other than the one end side and the other end side of the first flow channel, and the portion of the second flow channel is a middle portion of the first flow channel other than the one end side and the other end side of the second flow channel.

14. A semiconductor micro-analysis chip apparatus, comprising:
the semiconductor micro-analysis chip of claim 11;
a package configured to contain the semiconductor microchip;
a sample liquid inlet port provided on the first absorber and the second absorber of the package; and
a partition plate provided at the sample liquid inlet port and configured to supply the sample liquid introduced to the sample liquid inlet port separately to the first absorber and the second absorber.

15. The apparatus of claim 14, further comprising a particle size filter arranged in one of the first flow channel and the second flow channel, the particles passing through or being collected by the particle size filter.

16. The apparatus of claim 14, wherein the first flow channel and the second flow channel are groove-shaped tunnel-like flow channels each comprising a groove provided in the semiconductor substrate.

17. The apparatus of claim 14, wherein:
each of the first flow channel and the second flow channel is a stack-shaped tunnel-like flow channel which forms a hollow structure provided on the semiconductor substrate.

* * * * *